(12) United States Patent
Condeelis et al.

(10) Patent No.: US 12,055,547 B2
(45) Date of Patent: Aug. 6, 2024

(54) TMEM ACTIVE TEST AND USES THEREOF IN DIAGNOSIS, PROGNOSIS AND TREATMENT OF TUMORS

(71) Applicant: Albert Einstein College of Medicine, Bronx, NY (US)

(72) Inventors: John S. Condeelis, Bronx, NY (US); Allison S. Harney, Bronx, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 411 days.

(21) Appl. No.: 17/209,670

(22) Filed: Mar. 23, 2021

(65) Prior Publication Data

US 2021/0223250 A1 Jul. 22, 2021

Related U.S. Application Data

(62) Division of application No. 15/573,498, filed as application No. PCT/US2016/033862 on May 24, 2016, now abandoned.

(60) Provisional application No. 62/166,730, filed on May 27, 2015.

(51) Int. Cl.
*G01N 33/574* (2006.01)
*C07K 16/22* (2006.01)

(52) U.S. Cl.
CPC ....... *G01N 33/57484* (2013.01); *C07K 16/22* (2013.01); *G01N 33/574* (2013.01); *C07K 2317/76* (2013.01); *G01N 33/57415* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | |
|---|---|---|
| 8,298,756 B2 | 10/2012 | Condeelis |
| 8,603,738 B2 | 12/2013 | Condeelis et al. |
| 8,642,277 B2 | 2/2014 | Condeelis et al. |
| 9,719,142 B2 | 8/2017 | Condeelis et al. |
| 2011/0059470 A1 | 3/2011 | Condeelis et al. |
| 2011/0296538 A1 | 12/2011 | Segall et al. |
| 2012/0322685 A1 | 12/2012 | Condeelis et al. |
| 2013/0004424 A1 | 1/2013 | Gertler et al. |
| 2014/0066319 A1 | 3/2014 | Gertler et al. |
| 2014/0314786 A1 | 10/2014 | Condeelis et al. |
| 2015/0044234 A1 | 2/2015 | Gertler et al. |
| 2015/0104442 A1 | 4/2015 | Condeelis et al. |

FOREIGN PATENT DOCUMENTS

WO 2015069266 A1 5/2015

OTHER PUBLICATIONS

Voura et al, Microsc Res Tech, 43:265-175, 1998.*
PCT International Search Report and Written Opinion dated Oct. 19, 2016 for PCT International Patent Application No. PCT/US2016/33862, 11 pages.
Pucci F et al., entitled "A distinguishing gene signature shared by tumor-infiltrating Tie2-expressing monocytes, blood "resident" monocytes, and embryonic macrophages suggests common functions and developmental relationships," Blood, Jul. 23, 2009, vol. 114, No. 4, 901-914.
Harney A S et al., entitled "Real-time imaging reveals local, transient vascular permeability and tumor cell intravasation stimulated by Tie2Hi macrophage-derived VEGFA," Cancer Discov. Sep. 2015; 5(9):932-943.
Dejana et al., "Vascular endothelial-cadherin and vascular stability", Curr Opin Hematol, 19:218-223, 2012.
Ma et al, "Extracellular matrix protein big-h3/TGFBI promotes metastasis of colon cancer by enhancing cell extravasation", Genes & Dev, 22:308-321, 2008.
Weis et al, "Endothelial barrier disruption by VEGF-mediated Src activity potentiates tumor cell extravasation and metastasis", J Cell Biol, 167:223-229, 2004.

* cited by examiner

*Primary Examiner* — Mark Halvorson
(74) *Attorney, Agent, or Firm* — Fox Rothschild LLP

(57) ABSTRACT

Disclosed are kits and methods for detecting the presence of tumor sites that are active in tumor cell dissemination and uses thereof for determining the risk of tumor cells undergoing hematogenous metastasis, for assessing the prognosis of a subject undergoing treatment for a localized tumor, for determining a course of treatment for a localized tumor, and for identifying agents to treat or prevent hematogenous metastasis.

3 Claims, 33 Drawing Sheets

TC/Macrophage/EC

Tumor cell/Macrophage/Dextran

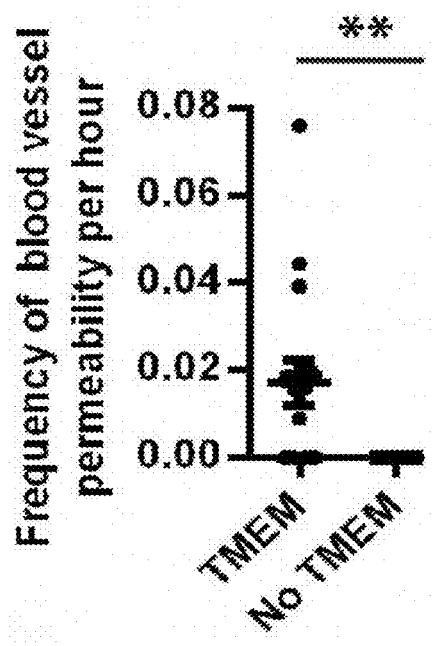
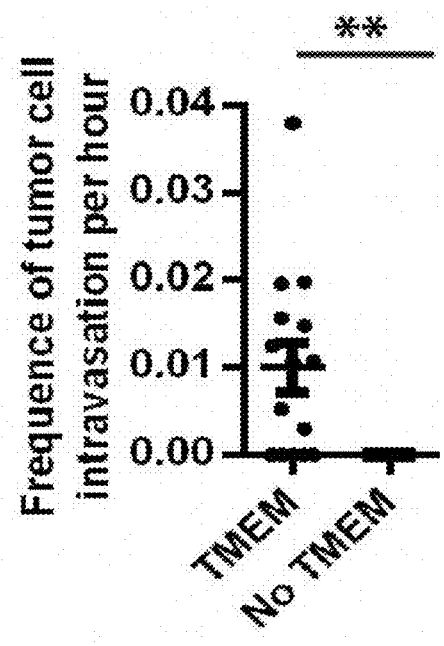
FIG. 1K                FIG. 1L
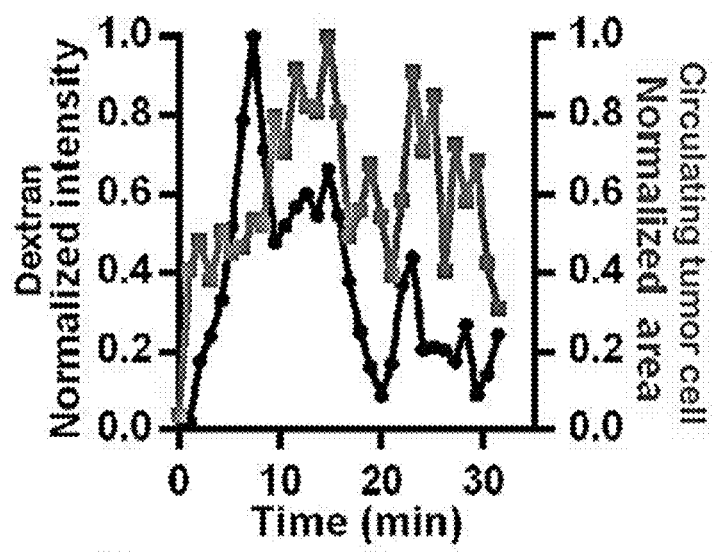
FIG. 1M $$f(t) = A\,e\left[\frac{-(t-\mu_1)}{\sigma_1}\right]erfc\left[\frac{-(t-\mu_2)}{\sigma_2}\right]$$

| Vessel leakiness | $\mu_1$ | $\sigma_1$ | $\mu_2$ | $\sigma_2$ |
|---|---|---|---|---|
| Spontaneous | 16.80 | 15.21 | 12.44 | 10.15 |
| VEGFA | 35.55 | 13.92 | 22.07 | 17.02 |
| Damage | N/A | N/A | 29.69 | 29.17 |

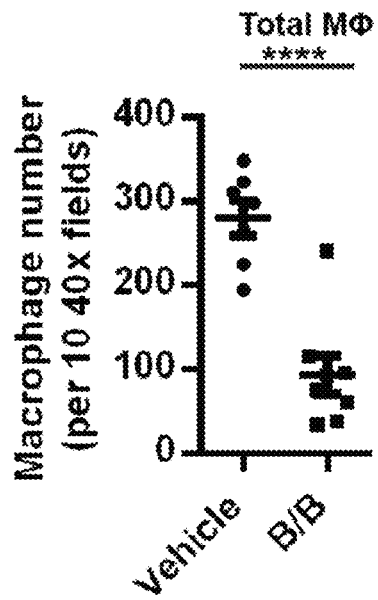
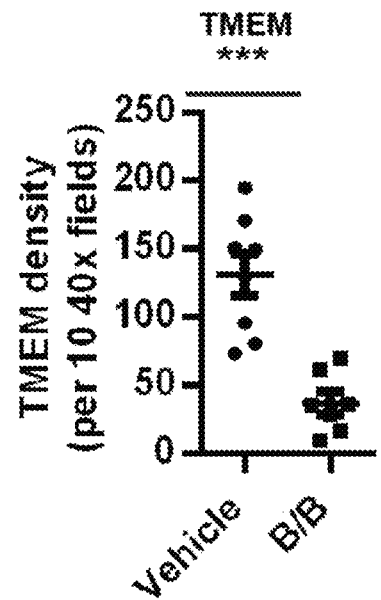
FIG. 2H    FIG. 2I
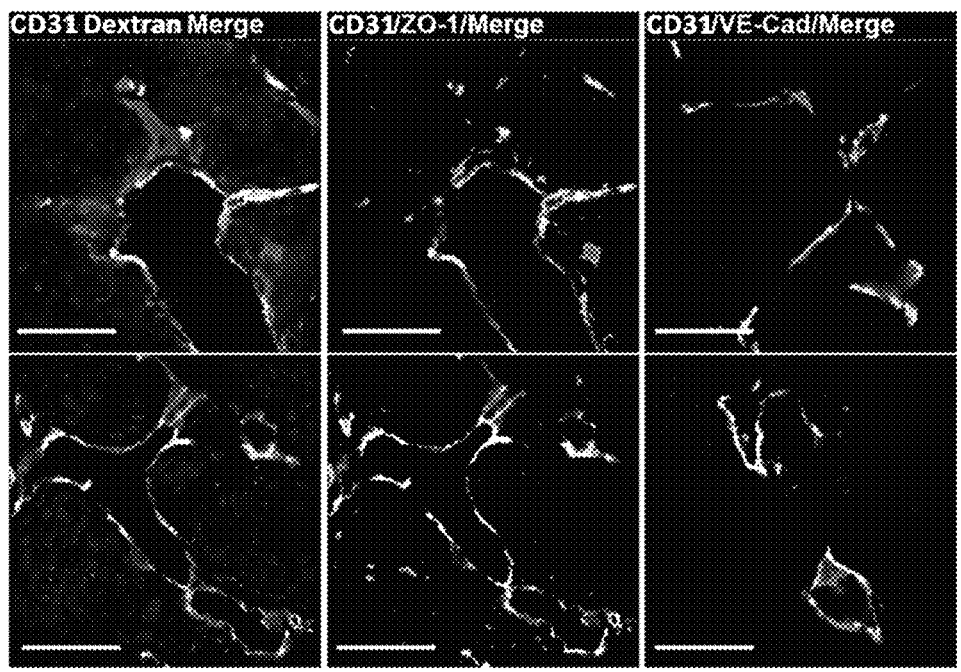
FIG. 2J

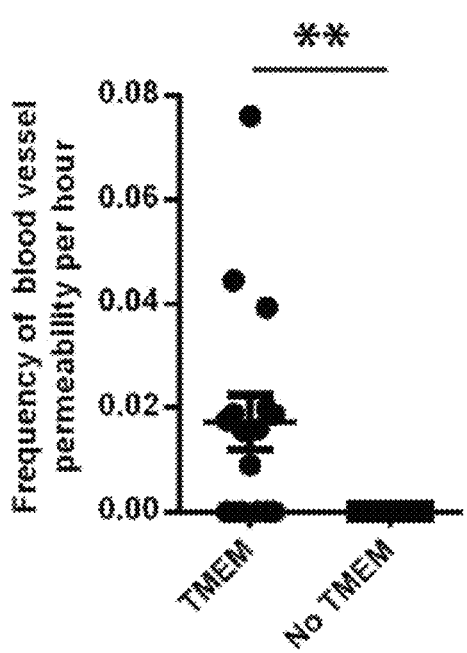
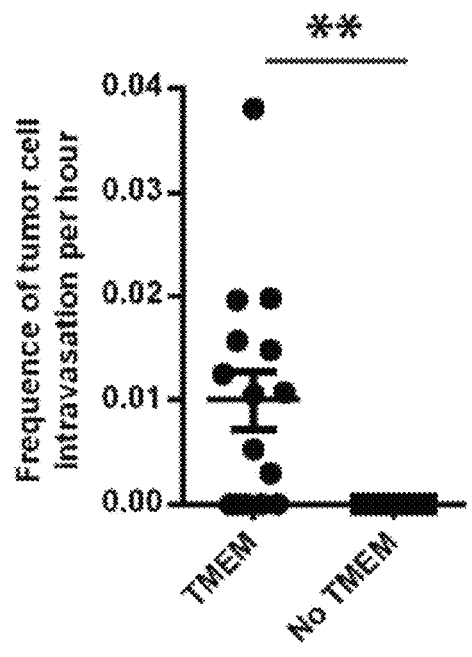
FIG. 5C
FIG. 5D
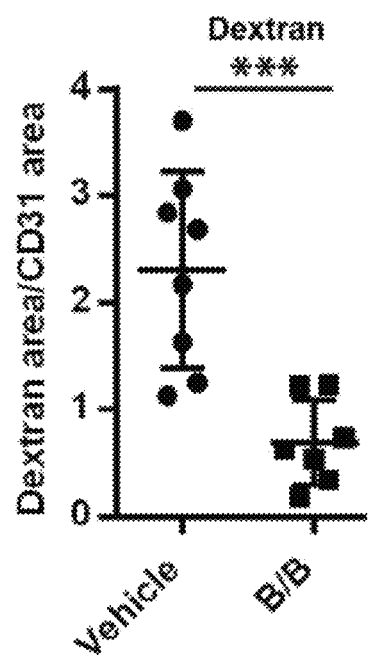
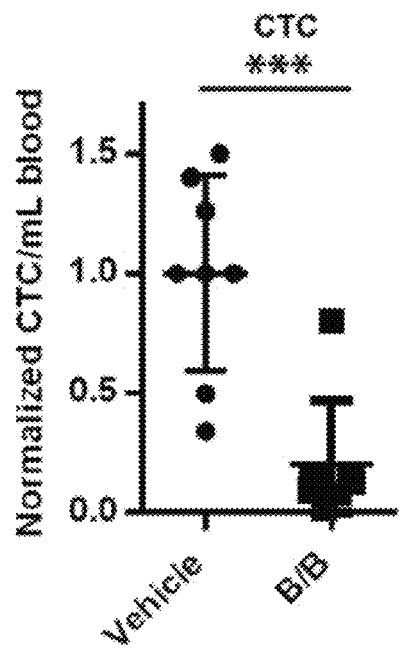
FIG. 5E
FIG. 5F

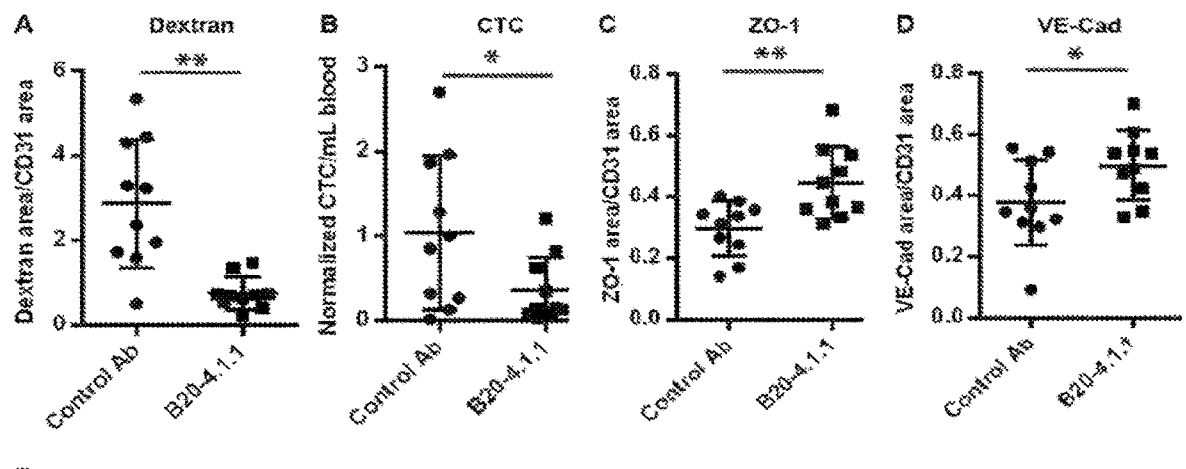
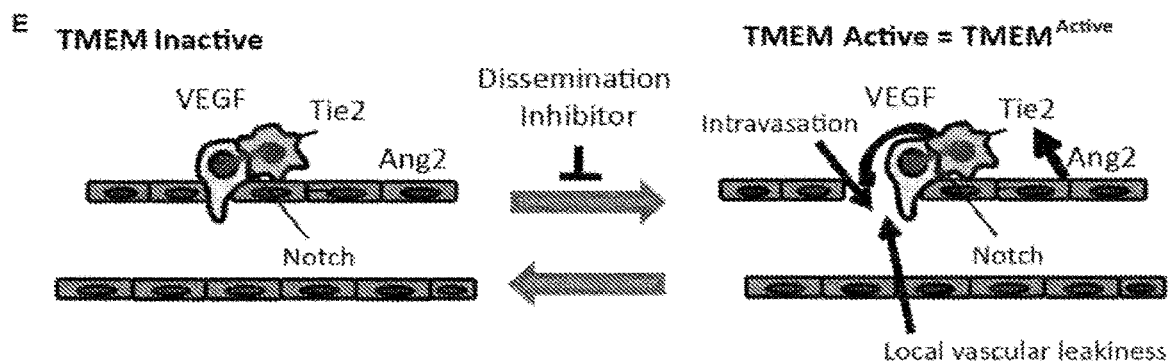
FIG. 8A - 8E

TMEM ACTIVE TEST AND USES THEREOF IN DIAGNOSIS, PROGNOSIS AND TREATMENT OF TUMORS

CROSS-REFERENCE TO RELATED APPLICATIONS

This application is a divisional of U.S. patent application Ser. No. 15/573,498, filed Nov. 13, 2017, which is a U.S. national stage under 35 U.S.C. § 371 of PCT International Patent Application No. PCT/US2016/033862, filed May 23, 2016, which claims the benefit of U.S. Provisional Patent Application No. 62/166,730, filed May 26, 2015, the contents of each of which are herein incorporated by reference.

STATEMENT OF GOVERNMENT SUPPORT

This invention was made with government support under grant number CA100324 awarded by the National Institutes of Health and grant number W81XWH-13-1-0010 awarded by the Department of Defense Breast Cancer Research Program. The government has certain rights in this invention.

BACKGROUND OF THE INVENTION

Various publications are referred to in parentheses throughout this application. Full citations for these references may be found at the end of the specification immediately preceding the claims. The disclosures of these publications are hereby incorporated by reference in their entireties into the subject application to more fully describe the art to which the subject application pertains.

For almost two decades tumor vasculature has been described as abnormal with increased vascular permeability (1, 2). Vascular endothelial growth factor A (VEGFA) is known to promote vascular permeability, and inhibition of VEGFA results in the normalization of tumor vasculature and a decrease in permeability (3, 4). Due to the significant effects of VEGFA on tumor angiogenesis and vascular permeability, inhibitors of VEGF signaling have become an important research focus in the development of anti-tumor therapies.

Tumor-associated macrophages (TAMs) have been implicated in tumor progression, angiogenesis and metastasis (5, 6). A subpopulation of perivascular TAMs that have features of pro-tumorigenic macrophages, promoting tumor angiogensis and metastasis, has been identified as Tie2-expressing macrophages (TEMs) (7). Perivascular macrophages are also an essential component of the microanatomical sites termed "tumor microenvironment of metastasis" (TMEM) that consist of a TAM in direct contact with a Mammalian enabled (Mena) over-expressing tumor cell and endothelial cell (8, 28). TMEM have been associated with tumor cell intravasation (9, 10) and TMEM density predicts distant metastatic recurrence in breast cancer patients independently of other clinical prognostic indicators (8, 11, 28). However, the mechanistic link between perivascular macrophages and tumor cell intravasation remained unclear. Further, hyperpermeability in tumor vasculature is not uniform, but rather is spatially and temporally heterogeneous (12). In a VEGFA overexpression model inducing vascular permeability, the presence of macrophages at vascular branch points was observed at hotspots of vascular permeability (4). Although hyperpermeability of tumor vasculature is widely accepted, a mechanistic understanding of the heterogeneity of vascular permeability, the contribution of TAMs, and the link with tumor cell intravasation has not been described.

There is a need for reliable methodologies to predict the risk for metastatic disease in cancer patients in order both to administer proper treatment to patients whose tumors have a high risk of metastasizing and to avoid unnecessary administration of chemotherapy to patients whose tumor had a negligible risk of metastasizing. The present invention addresses this need.

SUMMARY OF THE INVENTION

Provided are methods of determining the presence of one or more sites that are active in tumor cell dissemination in a subject, the methods comprising
  treating a tumor sample from the subject to detect Tie2, VEGFA, CD68, and VE-Cadherin and/or ZO-1, wherein the presence of CD68 indicates the presence of a macrophage, and
  detecting levels of Tie2, VEGFA, and VE-Cadherin and/or ZO-1,
  wherein $Tie2^{Hi}/VEGFA^{Hi}$ peri-vascular macrophages associated with low levels of VE-Cadherin and/or ZO-1 endothelial staining indicate the presence of sites that are active in tumor cell dissemination ($TMEM^{Active}$ sites), and
  wherein $Tie2^{Hi}/VEGFA^{Hi}$ peri-vascular macrophages associated with high levels of VE-Cadherin and/or ZO-1 endothelial staining indicate that there are no active sites of tumor cell dissemination.

Also provided are methods for determining the risk of tumor cells undergoing hematogenous metastasis comprising determining whether or not a tumor sample from a subject contains $TMEM^{Active}$ sites, wherein the risk of tumor cells undergoing hematogenous metastasis increases with the presence of $TMEM^{Active}$ sites.

Still further provided are methods for determining a course of treatment for a tumor in a subject, the method comprising determining whether or not a tumor sample from a subject contains $TMEM^{Active}$ sites, wherein the presence of $TMEM^{Active}$ sites indicates that the subject should be treated for a metastatic tumor or wherein a lack of $TMEM^{Active}$ sites indicates that the subject does not need to be treated for a metastatic tumor.

Also provided is a method for assessing the efficacy of an anti-cancer therapy in inhibiting tumor cell dissemination and metastasis in a subject comprising assaying a tumor sample from the subject for the presence of TMEM Active sites by the method disclosed herein, wherein a reduction of $TMEM^{Active}$ sites in the subject undergoing anti-cancer therapy indicates that the anti-cancer therapy is effective and wherein a lack of reduction of $TMEM^{Active}$ sites in the subject undergoing anti-cancer therapy indicates that the anti-cancer therapy may not be effective.

A method of preventing or reducing tumor cell dissemination and metastasis in a subject is provided, where the method comprises:
  a) receiving an identification of the subject as having tumor sites that are active in tumor cell dissemination by the method disclosed herein; and
  b) administering an anti-cancer therapy to the subject identified as having tumor sites that are active in tumor cell dissemination.

Still further provided are methods for identifying agents to treat or prevent hematogenous metastasis, the methods comprising contacting tumor samples with the agent and analyzing whether or not the agent reduces the number of TMEM$^{Active}$ sites, wherein an agent that reduces the number of TMEM$^{Active}$ sites is a candidate agent for treating or preventing hematogenous metastasis.

BRIEF DESCRIPTION OF THE DRAWINGS

FIG. 1A-1M. Transient, local blood vessel permeability events accompany intravasation, at TMEM. (A) Time 0' in the left panel indicating TMEM (white box) from time-lapse IVM. Macrophages (M), Tumor cells (TC) and blood vessels (155 kDa Dextran-TMR). Single time point of tumor cell and macrophage streaming towards non-migratory TMEM (asterisk). Streams and TMEM are in different focal planes. Scale bar, 50 µm. (B) 3D reconstruction of time-lapse IVM from (A) of TC and macrophage streaming towards TMEM (asterisk). Scale bar, 20 µm. (C) 3D reconstruction of TC intravasation (arrowhead) at TMEM (luminal surface of the endothelium dashed white line). (D) IVM time-lapse of tumor cell intravasation at TMEM. TC arrives at TMEM (arrowhead) and undergoes transendothelial migration (arrow) while TMEM macrophage and TC remain relatively immobile. Scale bar=10 µm. (E) Schematic summary diagram of panels A-D where TC (T2) and macrophage (M2) stream towards non-migratory TMEM (box, T1 and M1), where the TC (T2) undergoes transendothelial migration. (F) IVM time-lapse of 155 kDa dextran-TMR extravasation and tumor cell intravasation. TMEM (white box). Blood vessel permeability sites (arrowheads) and intravasating TC (dotted line, 9'). Clearance of dextran and decrease of CTC at 30'. Scale bar, 50 µm. At 9' and 30' TMEM tumor cells and macrophages are added in false color to increase visibility after bleaching. (G) Isolated 155 kDa dextran-TMR channel from F. Arrows mark dextran extravasation (white). Dashed line indicates the luminal side of the endothelium. (H) Isolated tumor cell channel from (F). Arrowhead marks site of intravasating TC (dashed line) at TMEM. White dashed line marks the luminal surface of the endothelium. Box indicates the region adjacent to TMEM with elevated CTC. (I) Single time point of tumor cell intravasation (dashed line) by time-lapse IVM. Scale bar, 50 µm. (J) 3D reconstruction of time-lapse IVM from I of tumor cell intravasation at TMEM. Transmigrating tumor cells (individually numbered, dashed white lines) are isolated from other cell types for clarity with time in minutes from start (J0') to end of transmigration (J3'). The luminal endothelial surface is outlined in a dashed line. Extravascular dextran at TMEM indicated with an arrowhead. (K) Frequency of blood vessel permeability events in the presence of TMEM or away from TMEM in 100 µm windows (n=16, , P=0.0034). (L) Frequency of tumor cell intravasation events in the presence of TMEM or away from TMEM in 100 µm windows (n=16, , P=0.0012). (M) Quantification of extravascular dextran intensity and CTC area at TMEM over time from F. (●) Extravascular dextran, (■) CTC.

FIG. 5A-5H. Tumor cell intravasation and transient blood vessel permeability occur exclusively at TMEM. (A) Intravital imaging microscopy time-lapse of tumor cell intravasation at TMEM. TMEM is composed of a tumor cell (TC), macrophage (M) and endothelial cell (EC) in direct contact. Another tumor cell (arrowhead) from the stream behind appears adjacent to TMEM and undergoes transendothelial migration (arrow). Scale bar=10 µm. (B) 3D reconstruction of TMEM from live tumor time lapse. Tumor cells approaching the blood vessel in a stream are indicated by arrowheads. The TMEM macrophage (M), tumor cell (TC) and their associated blood vessel endothelial cell (EC) are indicated with arrows. The TMEM-associated tumor cell (TC) does not move while the streaming tumor cells (arrowheads) approach and intravasate at TMEM. Scale bar=5 µm. (C) Frequency of blood vessel permeability events in the presence of TMEM or absence of TMEM per imaging field. (D) Frequency of tumor cell intravasation events in the presence of TMEM or absence of TMEM per imaging field. (E-H) Macrophage depletion in PyMT tumors in the MAIFA (macrophage fas– induces apoptosis) mouse model reduces blood vessel permeability and tumor cell intravasation. (E) Quantification of extravascular 155 kDa dextran-TMR (vehicle n=7, B/B homodimerizer-induced removal of macrophages, n=8; *, P=0.0009) (F) circulating tumor cells (*, P=0.0007) (G) Vascular ZO-1 (**, P=0.006) and (H) Vascular VE-Cadherin (* P=0.02).

FIG. 8A-8E. Inhibition of VEGFA reduces blood vessel permeability and tumor cell intravasation. Quantification in tumor sections after treatment with anti-VEGFA blocking antibody (B20-4.1.1) or IgG control antibody of (A) extravascular 155 kDa dextran-TMR and (n=10; **, P=0.0015) (B) circulating tumor cells (*, P=0.0497), (C) Vascular ZO-1 (**, P=0.005) and (D) Vascular VE-Cadherin (*, P=0.0463). (E) Schematic diagram of TMEM activation leading to blood vessel permeability and tumor cell intravasation. At TMEM a tumor cell and macrophage interact with the endothelium. When Tie2$^{Hi}$ macrophage of TMEM signals with elevated VEGF, endothelial cell junction remodeling occurs through VEGF signaling. Vascular junctions are degraded leading to decreased VE-Caderhin and ZO-1 in CD31+ endothelial cells resulting in increased vascular leakiness. Increased vascular permeability supports tumor cell intravasation at TMEM sites.

DETAILED DESCRIPTION OF THE INVENTION

Provided is a method of determining the presence of one or more sites that are active in tumor cell dissemination in a subject, the method comprising
  treating a tumor sample from the subject to detect Tie2, VEGFA, CD68, CD31, and VE-Cadherin and/or ZO-1, wherein the presence of CD68 indicates the presence of a macrophage and wherein the presence of CD31 indicates the presence of an endothelial cell, and
  analyzing levels of Tie2, VEGFA, and VE-Cadherin and/or ZO-1,
  wherein $Tie2^{Hi}/VEGFA^{Hi}$ peri-vascular macrophages associated with low levels of VE-Cadherin and/or ZO-1 endothelial staining indicate the presence of sites that are active in tumor cell dissemination (TMEM Active sites), and wherein $Tie2^{Hi}/VEGFA^{Hi}$ peri-vascular macrophages associated with high levels of VE-Cadherin and/or ZO-1 endothelial staining indicate that there are no sites that are active in tumor cell dissemination.

$Tie2^{Hi}/VEGFA^{Hi}$ CD68+ cells in direct contact with a blood vessel identify the presence of a TMEM site (see Experimental Details below). TMEM Active sites are TMEM sites that are active in tumor cell dissemination.

Also provided is a method for determining the risk of tumor cells undergoing hematogenous metastasis comprising assaying a tumor sample from a subject for the presence of TMEM Active sites by the method disclosed herein, wherein the risk of tumor cells undergoing hematogenous metastasis increases with the presence of $TMEM^{Active}$ sites.

Still further provided is method for determining a course of treatment for a tumor in a subject comprising assaying a tumor sample from the subject for the presence of TMEM Active sites by the method disclosed herein, wherein the presence of $TMEM^{Active}$ sites indicates that the subject should be treated for a metastatic tumor or wherein a lack of $TMEM^{Active}$ sites indicates that the subject does not need to be treated for a metastatic tumor.

Also provided is a method for assessing the efficacy of an anti-cancer therapy in inhibiting tumor cell dissemination and metastasis in a subject comprising assaying a tumor sample from the subject for the presence of TMEM Active sites by the method disclosed herein, wherein a reduction of $TMEM^{Active}$ sites in the subject undergoing anti-cancer therapy indicates that the anti-cancer therapy is effective and wherein a lack of reduction of $TMEM^{Active}$ sites in the subject undergoing anti-cancer therapy indicates that the anti-cancer therapy may not be effective.

A method of preventing or reducing tumor cell dissemination and metastasis in a subject is provided, where the method comprises:

a) receiving an identification of the subject as having tumor sites that are active in tumor cell dissemination by the method disclosed herein; and
  b) administering an anti-cancer therapy to the subject identified as having tumor sites that are active in tumor cell dissemination.

Figures 11A, 11B:
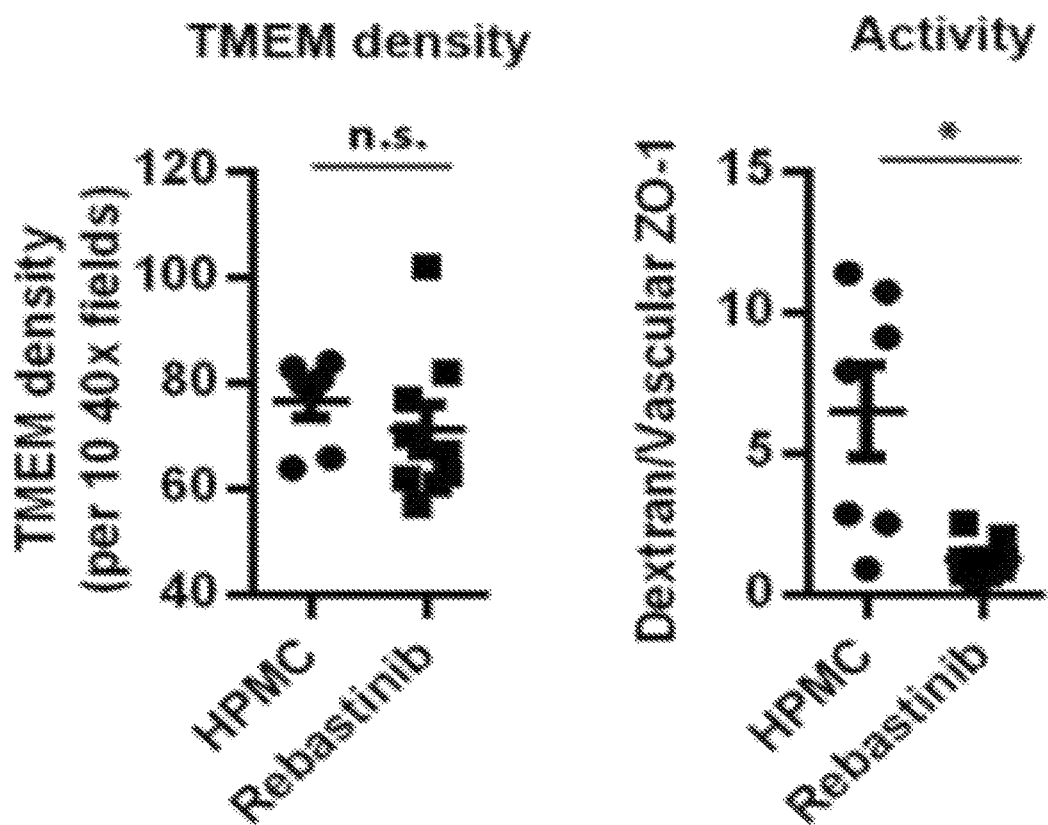
FIG. 11A-11B. Rebastinib, an inhibitor of Tie2 macrophage function in TMEM, inhibits TMEM activity. (A) Quantification of TMEM density in 10 40× fields (not significant). (B) Quantification of vascular permeability activity of tumor TMEM using vascular permeability marker IV-dextran/ZO-1 staining intensity (n=7 and 9; *, P=0.0177).

Preferably, the anti-cancer therapy comprises administration to the subject of a drug that inhibits TMEM function. The anti-cancer therapy can comprise administration of a Tie2 kinase inhibitor to the subject. Rebastinib is an example of a Tie2 kinase inhibitor (32, 33). FIG. 11 illustrates that rebastinib, an inhibitor of Tie2 macrophage function in TMEM, inhibits TMEM activity.

Still further provided is a method for identifying an agent to treat or prevent hematogenous metastasis, the method comprising contacting a tumor sample with the agent, assaying the tumor sample for the presence of TMEM Active sites by the method disclosed herein, and analyzing whether or not the agent reduces the number of $TMEM^{Active}$ sites, wherein an agent that reduces the number of $TMEM^{Active}$ sites is a candidate agent for treating or preventing hematogenous metastasis. In different embodiments, the tumor is contacted with the agent in vivo or ex vivo.

Also provided is a kit for detecting the presence of tumor sites that are active in tumor cell dissemination, the kit comprising reagents to detect one or more of Tie2, VEGFA, CD68, CD31, and VE-Cadherin and/or ZO-1. The reagent can be, for example, an antibody, an antibody fragment, a peptide or an aptamer. Antibody fragments include, but are not limited to, $F(ab')_2$ and Fab' fragments and single chain antibodies. The kit can further comprise instructions for a procedure to detect the presence of tumor sites that are active in tumor cell dissemination.

In any of the methods or kits disclosed herein, the tumor can be, for example, a secretory epithelial tumor. The tumor can be, for example, a prostate, pancreas, colon, brain, liver, lung, head or neck tumor, or in particular a breast tumor.

The present invention is illustrated in the following Experimental Details section, which is set forth to aid in the understanding of the invention, and should not be construed to limit in any way the scope of the invention as defined in the claims that follow thereafter.

Experimental Details

Introduction and Overview
  Dissemination of tumor cells from the primary tumor is an essential step in metastasis. Direct contact between a macrophage, tumor and endothelial cell [Tumor MicroEnvironment of Metastasis (TMEM)], correlates with metastasis. As disclosed herein, it is shown using intravital high-resolution two-photon microscopy, that transient vascular permeability and tumor cell intravasation occur simultaneously and exclusively at TMEM. The hyperpermeable nature of tumor vasculature has been described as spatially and temporally heterogeneous. Using real-time imaging it was observed that vascular permeability is transient, restricted to TMEM sites, and required for tumor cell dissemination. VEGFA signaling from $Tie2^{Hi}$ TMEM macrophages causes local loss of vascular junctions, resulting in transient vascular permeability and tumor cell intravasation, demonstrating a role for TMEM within the primary mammary tumor. These data provide insight into the mechanism of tumor cell intravasation and vascular permeability in breast cancer, and explain the prognostic value of TMEM density as a predictor of distant metastatic recurrence in patients.

Tumor vasculature is abnormal with increased vascular permeability. VEGFA signaling from Tie2$^{Hi}$ TMEM macrophages results in transient permeability and tumor cell intravasation at tumor blood vessels proximal to TMEM, explaining the previously unresolved heterogeneity in vascular permeability. These data provide evidence for the mechanism underlying the association of TMEM with distant metastatic tumor recurrence in mouse models and human breast cancer patients, offering a rationale for the development of therapeutic approaches targeting TMEM formation and function.

Materials and Methods

Summary Tumor cell intravasation at sites of transient vascular permeability associated with TMEM was studied using mouse mammary tumor virus—polyoma middle T antigen (MMTV-PyMT) autochthonous and implanted models of human patient-derived mammary carcinoma. Single cell resolution of cell activity at TMEM in live animals was achieved using extended time-lapse imaging on a custom-built two-laser multiphoton microscope. To investigate the role of macrophages in tumor cell intravasation and blood vessel permeability, the MAFIA mouse model was used to deplete macrophages. Observation of extravascular dextran, vascular junction proteins and protein expression in tissue was performed using immunofluorescence microscopy. Further investigation of the mechanism of macrophage-mediated tumor cell intravasation and blood vessel permeability at TMEM utilized anti-mouse-VEGFA inhibitory antibody and the ablation of Vegfa expression in monocytes using a myeloid-specific (Csf1r promoter), tamoxifen-inducible Cre expressing mouse strain was crossed with Vegfa$^{flox/flox}$ mice with gene ablation induced with tamoxifen.

Tumor staging in PyMT. Early carcinoma and late carcinoma tumors were characterized by a pathologist according to previously characterized features (13). Briefly, early carcinoma tumors were used from PyMT mice 7-9 weeks old that are characterized by distended acinar structures with focal stromal invasion, high density of leukocytic infiltration, and increased cytological atypia and late carcinoma tumors from mice 12-14 weeks old that are characterized by solid sheets of epithelial cells with little or no remaining acinar structures visible (13).

Immunofluorescence image analysis. To measure vascular junctions and extravascular dextran, the CD31 channel (blood vessel), dextran and vascular junction (ZO-1 or VE-Cadherin) were each thresholded to just above background based upon intensity. Thresholding was verified by eye. A binary mask of the blood vessels was created to define the boundaries of the signal inside blood vessels. Structures smaller than 100 px$^2$ were excluded as debris, and holes were filled. The extravascular dextran area was isolated by subtracting the blood vessel mask from the dextran mask. The remaining extravascular dextran area, and blood vessel area were then measured. To measure vascular junction area the vascular junction image was thresholded to just above background in the blood vessel using the blood vessel mask and a binary mask was made of the vascular junction area. The area of vascular junctions and extravascular dextran was normalized to the area of blood vessels in each image.

Vascular VE-Cadherin adjacent to TMEM was quantified by the mean VE-Cadherin staining intensity in CD31+ vasculature adjacent to CD68+/Tie2$^{Hi}$/VEGFA$^{Hi}$ macrophages, CD68+ macrophages or in the absence of macrophages in sequential tissue sections. Four different fields (of 2×2 40× fields with 15% overlap) were acquired per mouse. To measure vascular VE-Cadherin, the CD31 channel (blood vessel), VEGFA and VE-Cadherin were each thresholded to just above background based upon intensity. Thresholding was verified by eye. A binary mask of the blood vessels was created to define the boundaries of the signal inside blood vessels. A box (ROI) was moved along the vasculature in 0.5 μm lengths of vasculature in a sliding window fashion as defined by a freehand drawn line. Average pixel intensity was measured in each of the CD31, VE-Cadherin and VEGFA channels for each ROI and moved along another 0.5 μm lengths of vasculature. Measurements were repeated until the end of the length (25 μm) of the line drawn. This method was adapted for use in measuring NG-2 staining intensity as a measure of pericyte coverage of vasculature. Pericyte coverate adjacent to TMEM was quantified by the mean NG-2 staining intensity in CD31+ vasculature adjacent to CD68+/CD206+/VEGFA$^{Hi}$ macrophages, CD68+ macrophages or in the absence of macrophages in sequential tissue sections. Four different fields (of 2×2 40× fields with 15% overlap) were acquired per mouse. To measure perivascular NG-2, and the CD31 channel (blood vessel), were thresholded to just above background based upon intensity. Thresholding was verified by eye. A box (ROI) was moved along the vasculature in 0.5 μm lengths of vasculature in a sliding window fashion as defined by a freehand drawn line. Average pixel intensity was measured in each of the CD31 and NG-2 channels for each ROI and moved along another 0.5 μm lengths of vasculature. Measurements were repeated until the end of the length (25 μm) of the line drawn. Average pixel intensity in NG-2 was determined for each length of vasculature measured and averaged for each animal.

To measure vascular VE-cadherin in human samples, the vasculature was outlined by CD31 staining in the IHC section. The ROI was applied to the VE-cadherin fluorescence channel and average signal intensity measured. Regions of vasculature adjacent to CD68/Tie2$^{Hi}$/VEGFA$^{Hi}$ macrophages or away from TMEM are measured (n=23 at TMEM, n=24 away from TMEM) in 5 independent patient samples.

Intravital imaging. Z-stacks of up to 50 μm of depth were acquired with a 2 μm slice interval for up to 4 h. Three time frames were acquired after the injection of 155 kDa TMR-dextran before the administration of 1.5 mg of 10 kDa fluorescein-dextran or 8 μg (0.2 mg/kg) of VEGFA$_{165}$ peptide (PeproTech) by the tail vein catheter to induce systemic vascular permeability as previously described (29, 30). For laser-induced damage, the laser was held at a position on the endothelium at 200 mW for 2 s (generating 400 mJ) after injection of 155 kDa-dextran-TMR. Extended time-lapse images were acquired.

Figure 2A:
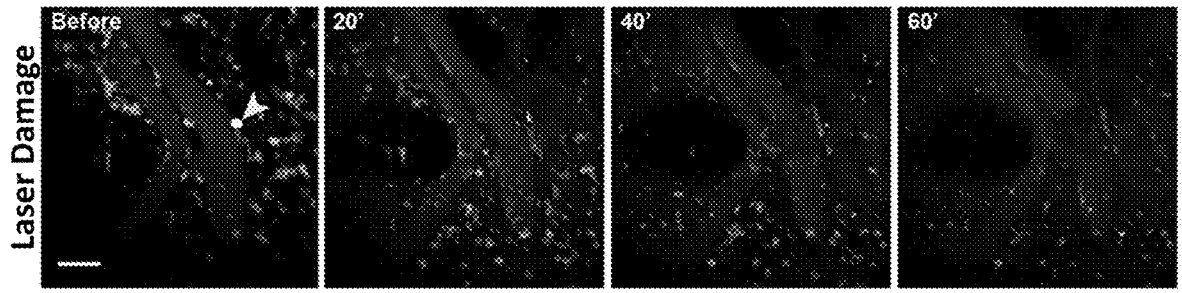
FIG. 2A-2N. Macrophage depletion reduces vascular permeability and tumor cell intravasation. (A) Time lapse imaging demonstrates that laser-induced damage to the endothelium creates a hole allowing for extravasation of 155 kDa dextran-TMR. The location of the hole is marked by a white dot (2 µm) and an arrowhead. 155 kDa dextran-TMR extravasates and increases over time up to 60' filling the field of view and not clearing from the tissue (n=4). Scale bar, 50 µm. (B) 155 kDa dextran-TMR is injected by tail vein i.v. catheter followed by 8 µg of VEGFA$_{165}$ at 0'. VEGFA$_{165}$ induces blood vessel permeability in all of the blood vessels in the field of view. Peak extravascular dextran is observed at 20' followed by clearance by 60' after rescaling of vascular junctions (n=4). Scale bar, 50 µm. (C) Spontaneous vascular permeability at TMEM is both transient and local. Local peak extravasation of 155 kDa dextran-TMR occurs after 20' (arrowhead) and clears within 60' (n=11). Scale bar, 50 µm. (D) Quantification of total extravascular 155 kDa dextran-TMR area after laser-induced damage, i.v. injection of VEGFA$_{165}$ or spontaneous permeability at TMEM from individual animals represented in A, B and C. Peak of 155 kDa dextran-TMR area in spontaneous permeability at TMEM indicated with an arrowhead. (●) laser damage, (■) intravenous VEGFA$_{165}$ and (▲) spontaneous vascular permeability at TMEM. (E) Quantification of average relative intensity of extravascular 155 kDa dextran-TMR after (●) laser damage (n=4), (■) intravenous VEGFA$^1_{65}$ n=4 and (▲) spontaneous permeability (n=11). (F) Table of parameters from curve fitting to an Exponentially Modified Gaussian function using data from (E). (G) Immunofluorescence imaging of tumor sections stained for TMEM. Vasculature (CD31), tumor cells (Mena) and macrophages (CD68) and DAPI. TMEM are outlined in a white box. Scale bar, 20 µm. H-N are changes in parameter shown after removal of macrophages with the agent B/B. (H) Quantification of total CD68+ macrophages in tumor tissue (**, P<0.0001), (I) in TMEM (*, P=0.0003). (J) Immunfluorescence imaging of tumor sections stained for vasculature (CD31), 155 kDa dextran-TMR and DAPI, ZO-1 or VE-Cadherin as indicated. Scale bar, 50 µm. (K) Quantification of extravascular 155 kDa dextran-TMR (vehicle n=7, B/B homodimerizer n=8; *, P=0.0009) (L) circulating tumor cells (*, P=0.0007) (M) Vascular ZO-1 (**, P=0.006) and (N) Vascular VE-Cadherin (* P=0.02).
Figure 2B:
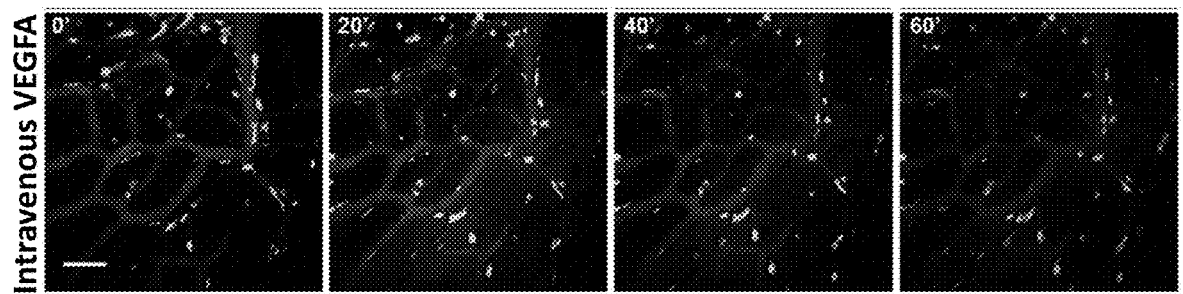

Intravital microscopy image analysis. All images were acquired as 16-bit TIFF images and all quantitative analysis was performed on the raw 16-bit TIFF images. As previously described, image channels were balanced and subtracted to isolate the CFP signal (31). An average intensity Z-projection was made for all channels. The ImageJ plug-in StackReg was used to register the images over time. The average intensity Z-projection is used for dextran analysis to determine quantitatively the mean dextran intensity within a volume of interest. The first image in the time-lapse sequence (t=0 min) was used to define the boundaries of the vasculature. Circular ROIs were placed adjacent to the vasculature in the tumor tissue at sites of spontaneous, transient vascular permeability. Average fluorescence intensity of dextran channel was measured in the ROI for each Z-projection time frame of the time-lapse sequence. Fluorescence intensity values were normalized to the maximum fluorescence intensity for each individual vascular permeability event. To determine the kinetics of transient vascular permeability (FIG. 2E), individual permeability events were aligned with 0 min determined as the first frame where dextran intensity increases above background. Individual permeability events were averaged to determine the average kinetics. For VEGFA$_{165}$ injection and laser damage experiments t=0 min is the start of image acquisition for all animals. To determine the total dextran area (FIG. 2D) a binary mask was made from the blood vessel signal within the first frame of the time-lapse sequence. The blood vessel mask was applied to all subsequent channels and subtracted from the dextran channel to measure only extravascular dextran. The dextran channel was intensity thresholded to just above background and verified by eye and the total area was measured. Maximum intensity Z-projection was made for the tumor cell channel to best highlight the cells and suppress background. To measure circulating tumor cells, time-lapse stacks were cropped to an area over the blood vessel immediately downstream of TMEM sites with extravasation of vascular probes. The blood vessel and tumor cell channels were intensity thresholded to just above background and verified by eye. A binary mask was made from the blood vessel signal within the first frame of the time-lapse sequence. This image was used to define intact blood vessels and determine the boundaries of what is intra- and extravascular for the rest of the time-lapse sequence. Structures smaller than 100 μm$^2$ were excluded as debris, and all holes were filled. The blood vessel mask was applied to the tumor cell channel which was then thresholded just above background to detect all circulating tumor cells. The area in the tumor cell channel was measured as the area of circulating tumor cells which was used as a surrogate measure of the number for circulating tumor cells as the area increases with number. The area is a conservative measurement of circulating tumor cells as it increases directly with the cell number and any inaccuracy would be cause by spatial overlap in cells that would result in reducing the total area of circulating tumor cells measured. The area of circulating tumor cells was measured in each image in the time-lapse sequence. The area of circulating tumor cells was normalized to the frame with the maximum area of circulating tumor cells. A single optical plane is presented in the figures unless otherwise described. For three-dimensional reconstructions, data was imported into Imaris software (BitPlane) for surface rendering.

Sliding window measurement of tumor cell intravasation and vascular permeability. In this measurement a 100 μm sized boxes, size chosen based on the size of a TMEM, are placed along the vessels consecutively in a FOV. Each box is then interrogated for the presence of TMEM, tumor cell intravasation and vascular permeability events. Time-lapse sequences of z-stacks are interrogated to examine vasculature in 3D.

Results

TMEM-associated tumor cells and macrophages are stationary in TMEM structures. To examine the functional role of TMEM in tumor cell dissemination, the spontaneous autochthonous mouse mammary cancer model was used where the mouse mammary tumor virus long terminal repeat drives the polyoma middle T antigen (MMTV-PyMT), in which tumors exhibit histology similar to human luminal breast cancer, and progress to metastasis (13). Immunohistochemistry (IHC) revealed that TMEM structures in mouse tumors have the same microanatomical structure as identified in humans (11). TMEM density increases with tumor progression with elevated TMEM scores in late carcinoma (LC) as compared to early carcinoma (EC) as seen by IHC though total perivascular macrophage (including macrophages not associated with tumor cells) density is not significantly different (13). High-resolution imaging demonstrates that in TMEM structures, tumor cells and macrophages extend protrusions but are relatively non-migratory and stay in direct contact over time.

Figure 1A:
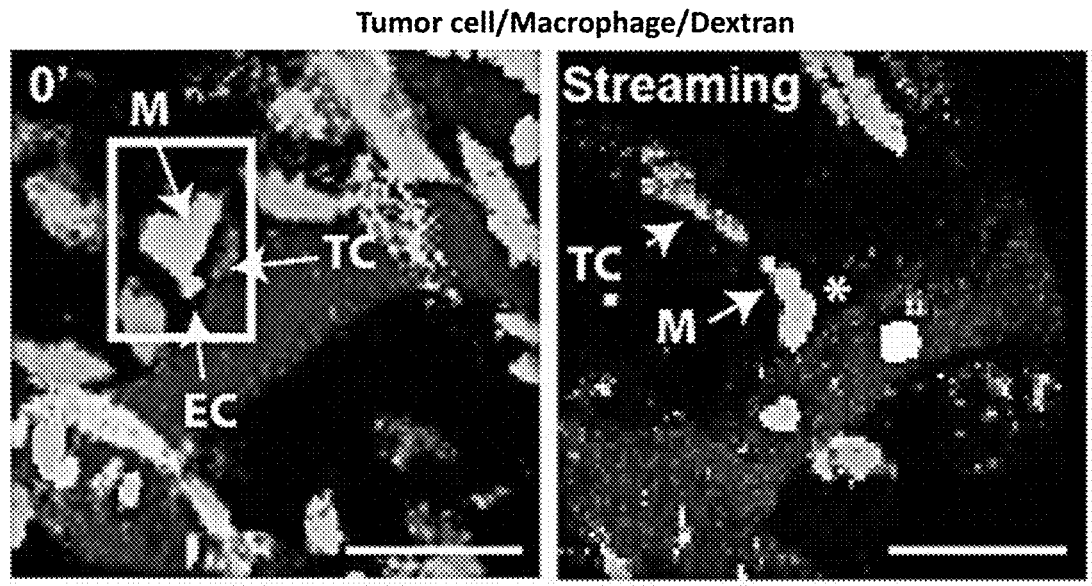
Figure 1B:
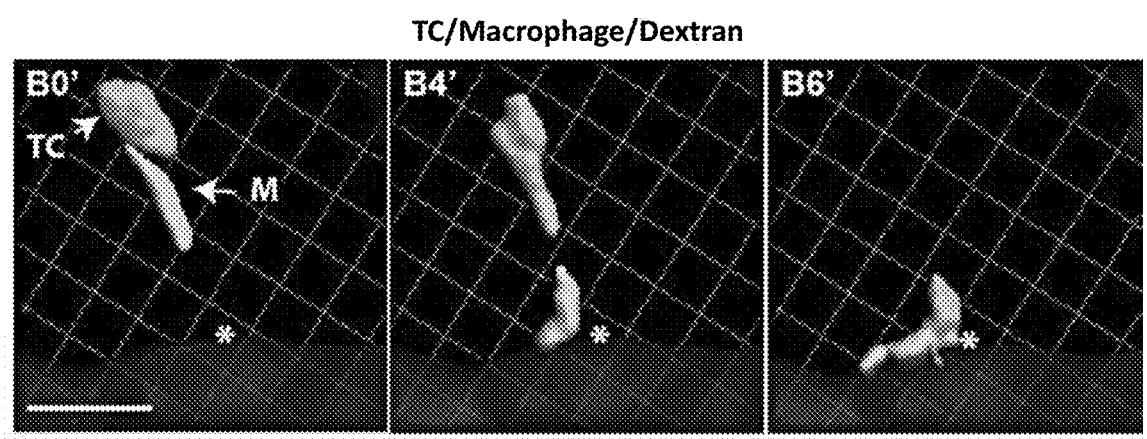
Figure 1C:
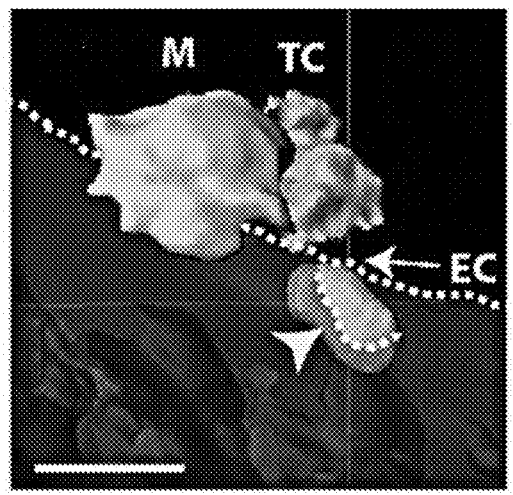
Figure 1D:
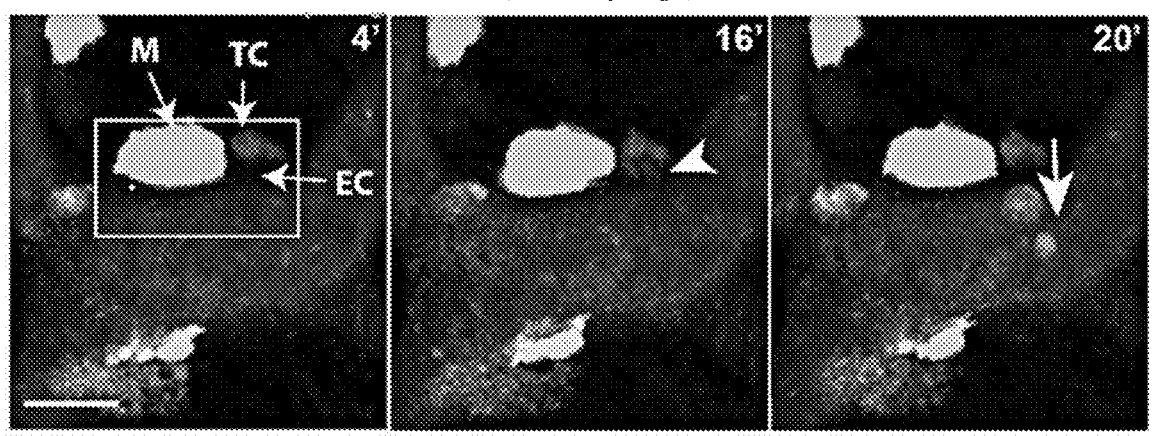
Figure 1E:
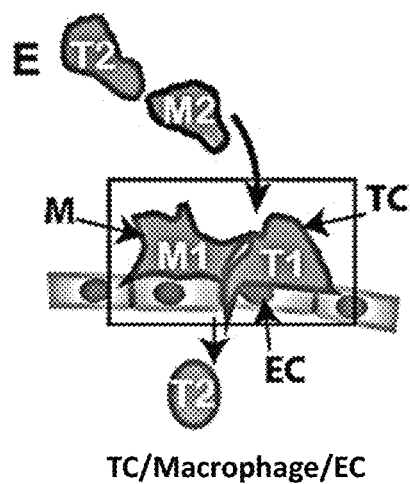
Figure 1F:
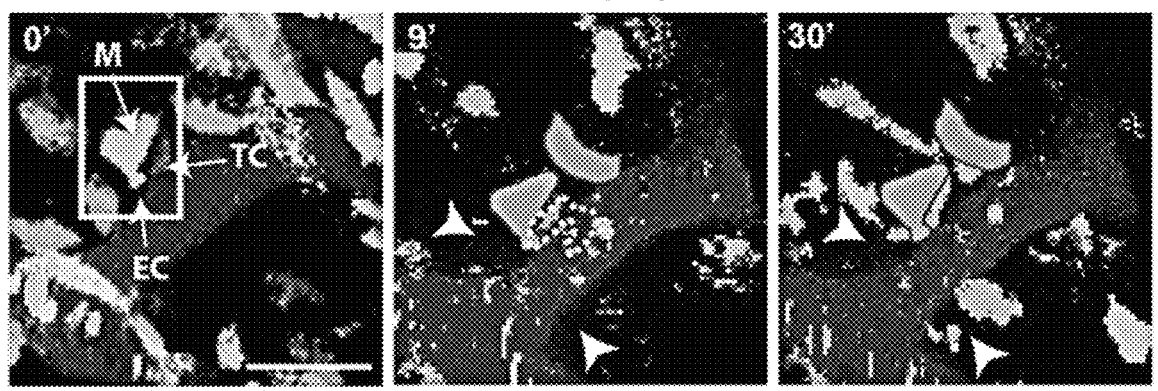
Figure 1G:
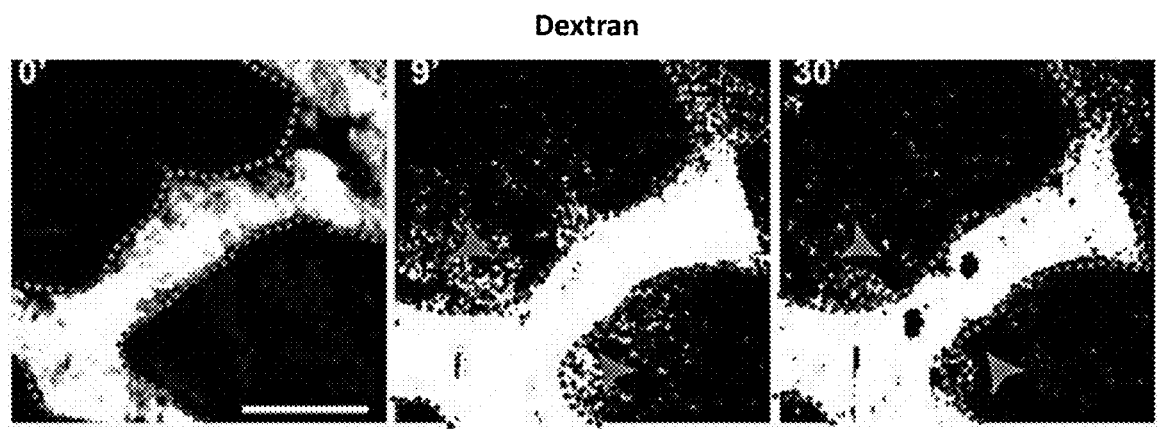
Figure 1H:
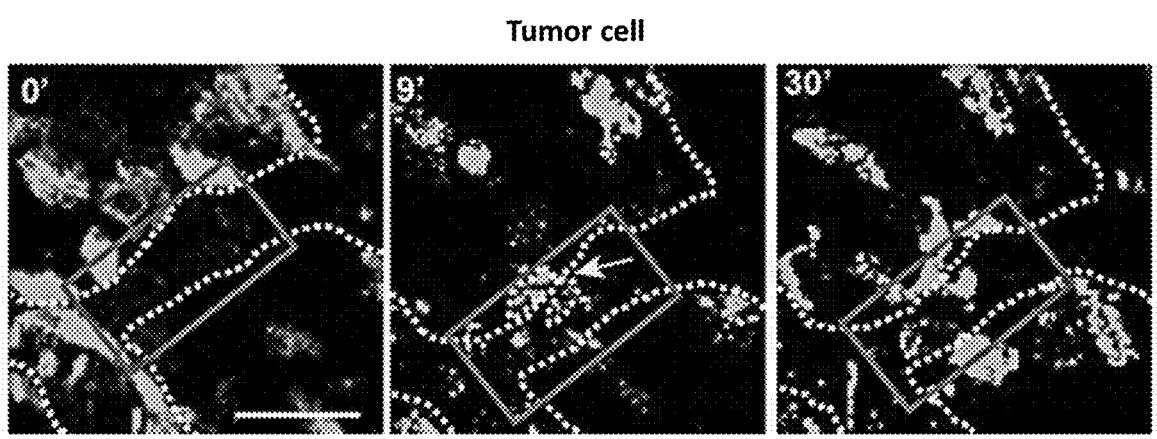
Figure 1I:
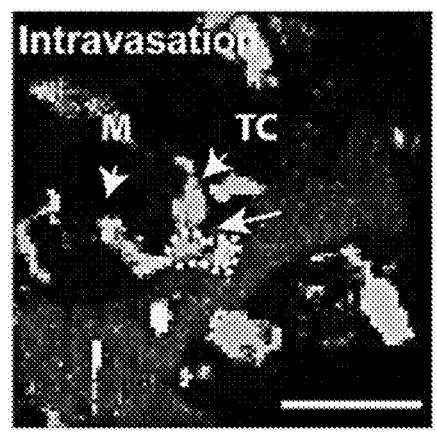
Figure 1J:
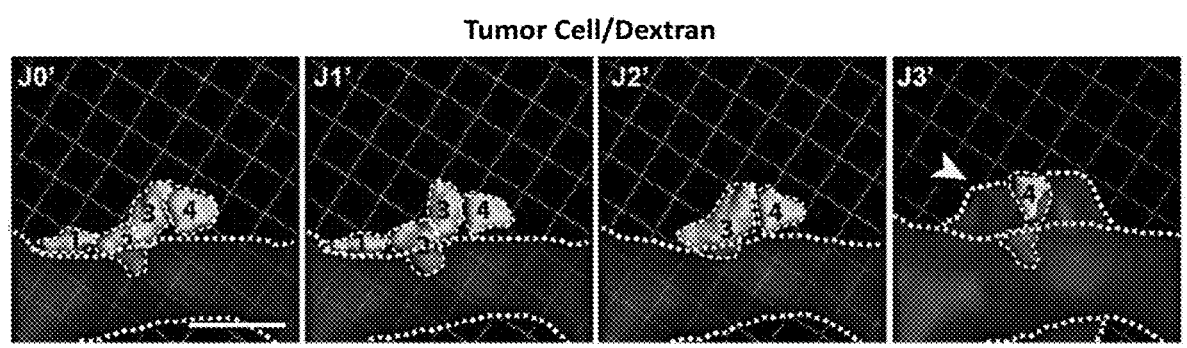

Vascular permeability and tumor cell intravasation occur concurrently at TMEM. To directly observe TMEM function in vivo, extended time-lapse intravital microscopy (IVM) with high spatial and temporal resolution was used. To visualize blood flow, vessels were labeled with a high molecular weight compound (155 kDa dextran or quantum dots) (1, 14) (FIG. 1). In LC, transient, local blood vessel permeability was observed at TMEM sites by the extravasation of quantum dots or 155 kDa dextran-tetramethylrhodamine (TMR) (FIG. 1F, G, K, 2C). In PyMT LC, tumor cell intravasation occurs at TMEM sites concurrently with transient permeability (FIG. 1M). Migratory tumor cells and macrophages stream towards TMEM at sites with vascular permeability whereupon tumor cells undergo transendothelial migration at TMEM (FIG. 1A-F, H-J). Transendothelial crossing of tumor cells is visualized by the hourglass shape of tumor cells as they are partially in the vessel lumen and partially in the tissue (FIG. 1C, F, H-J). During transendothelial migration of tumor cells, the TMEM tumor cell and macrophage neither migrate nor intravasate indicating that tumor cells entering the blood vessel at TMEM are supplied by the migratory stream of cells (FIGS. 1A, B and D). The stationary phenotype of these cells is consistent with previous results showing macrophage contact-initiated invadopodium formation uniquely in the TMEM tumor cell (9) and that perivascular invadopodium-containing tumor cells are relatively non-motile in vivo (15).

The peak of extravascular dextran intensity and the appearance of circulating tumor cells coincide temporally and spatially (FIGS. 1F-H, J, and M) demonstrating a direct link between localized blood vessel permeability and tumor cell intravasation at TMEM. The coincidence of spontaneous, transient vascular permeability with tumor cell intravasation at TMEM also has been observed in a patient-derived xenograft model of triple-negative breast cancer, TN1.

To confirm that TMEM is associated with transient vascular permeability and tumor cell intravasation a 100 μm window, the approximate width of a TMEM site, was consecutively slid along all blood vessels (window measurement) to quantify the frequency of tumor cell intravasation and vascular permeability events in the presence or absence of TMEM. Vascular permeability and tumor cell intravasation occur exclusively within the 100 μm window when it contains a TMEM, but never when the 100 μm window does not contain a TMEM in PyMT (FIGS. 1K and L). Similar results were observed in the human TN1 model highlighting the importance of TMEM in transient vascular permeability and tumor cell intravasation.

Figure 2C:
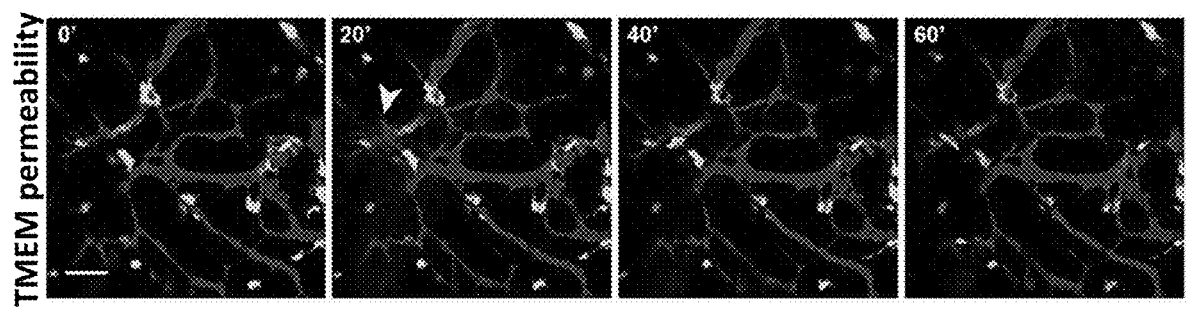
Figure 2D:
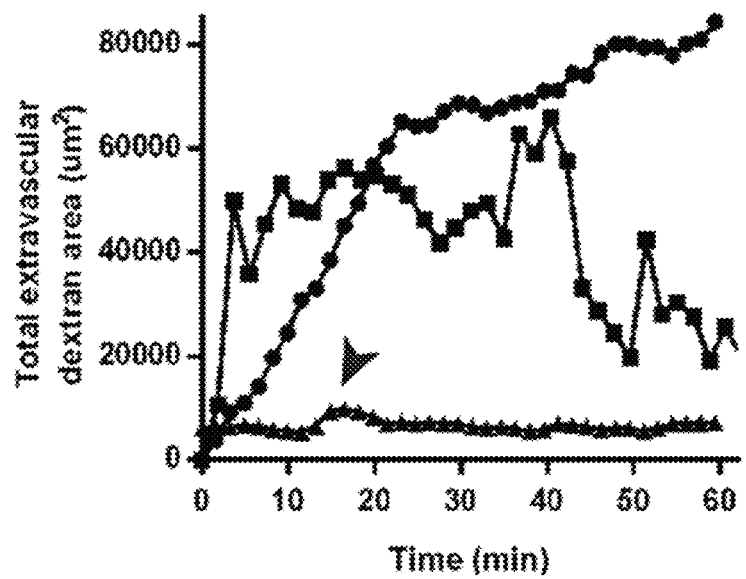

Vascular permeability at TMEM is a highly localized and transient event. Tumor vasculature has been previously described as abnormal with increased vascular permeability, which has been attributed to larger vascular intercellular openings (1, 12, 16). However, vascular permeability is not spatially or temporally uniform, with hotspots at vascular branch points (4, 12). Here it is demonstrated that vascular permeability is transient, occurs exclusively at TMEM sites, and is temporally heterogeneous, explaining the previously unresolved heterogeneity in vascular permeability (FIGS. 1K, 2C). Events of spontaneous, local vascular permeability and tumor cell intravasation at TMEM occur predominantly at vascular branch points, consistent with previous reports of vascular permeability. If tumor blood vessels were uniformly leaky high-molecular weight vascular probes would extravasate immediately and continuously after injection. While the high-molecular weight probe, 155 kDa dextran-TMR, remains in the vasculature in the absence of transient TMEM-associated permeability events for the duration of the time-lapse imaging, a low molecular weight dextran, 10 kDa dextran-fluorescein isothiocynate (FITC), below the molecular cutoff size of the endothelium (1, 14) leaks from blood vessels and clears from the vascular space.

Figure 2E:
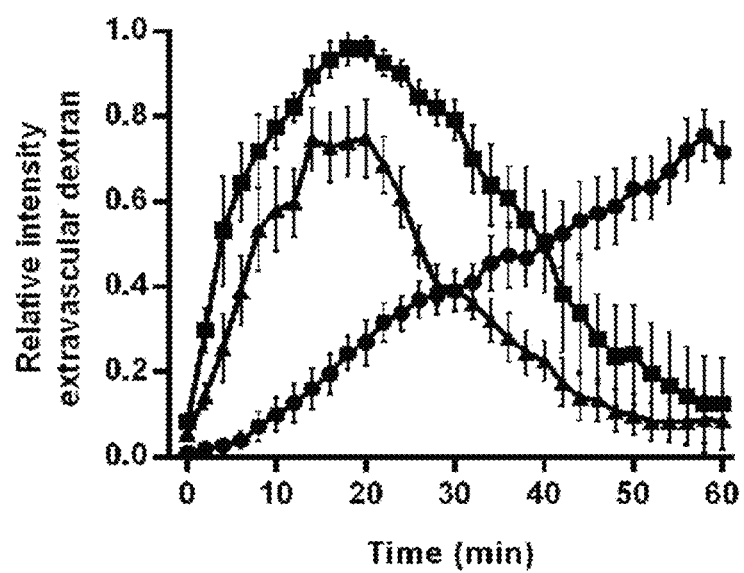

Further, transient permeability events are distinct from mechanical damage to the endothelium. After creating a 2 µm hole in the endothelium with a laser, 155 kDa dextran-TMR extravasates continuously, filling the field of view (FIG. 2A). By contrast, VEGFA-mediated permeability is transient (12). Intravenous injection of $VEGFA_{165}$, the soluble isoform of VEGFA with properties of native VEGF (17), results in vascular permeability with peak intensity of extravascular dextran at 20 min (FIG. 2B). Spontaneous vascular permeability at TMEM follows similar kinetics to $VEGFA_{165}$-mediated permeability with peak intensity of extravascular dextran at 20 min but is restricted to individual TMEM sites (FIG. 2C). The curves obtained for average intensity of extravascular 155 kDa dextran-TMR after laser damage, $VEGFA_{165}$ and spontaneous permeability were fit to an exponentially modified Gaussian function (FIGS. 2E and F). While the curve for laser damage does not have a clearance term as dextran continues to extravasate for the entire time-lapse, both the $VEGFA_{165}$ and spontaneous curves have similar extravasation and clearance rates. A significant difference between $VEGFA_{165}$ and spontaneous TMEM-mediated permeability is that permeability at TMEM is highly local, while $VEGFA_{165}$ results in dextran extravasation from all blood vessels within a field of view (FOV). Thus, the area of extravascular 155 kDa dextran-TMR from local TMEM-mediated permeability is markedly less than permeability from $VEGFA_{165}$ or laser-induced damage (FIG. 2D) further emphasizing the local nature of TMEM-mediated vascular permeability.

Figures 2F, 2G:
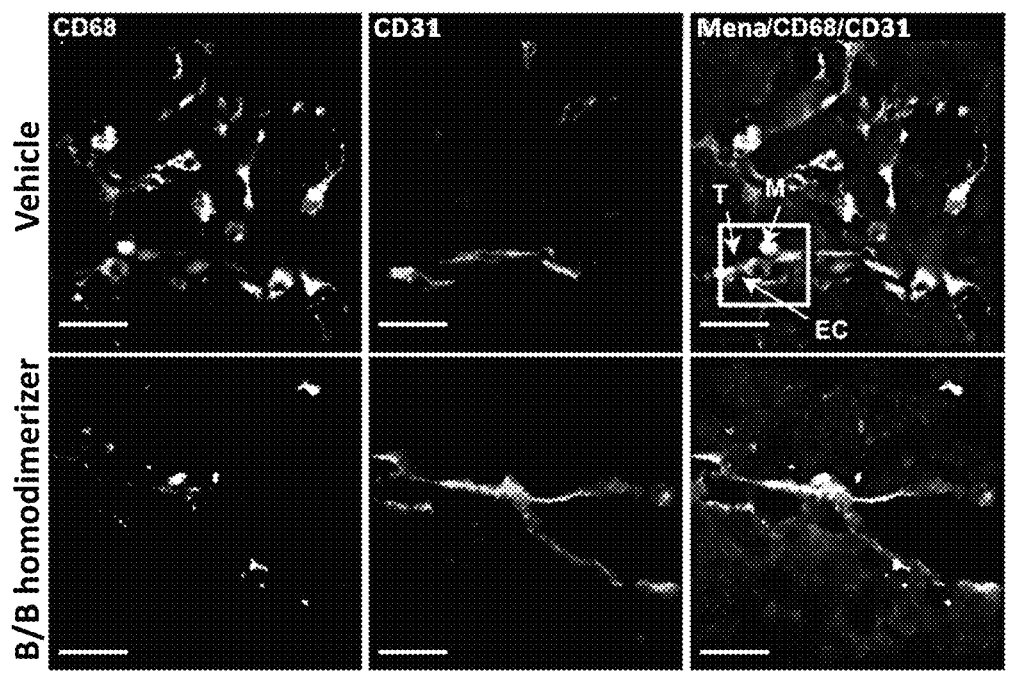
Figure 2K:
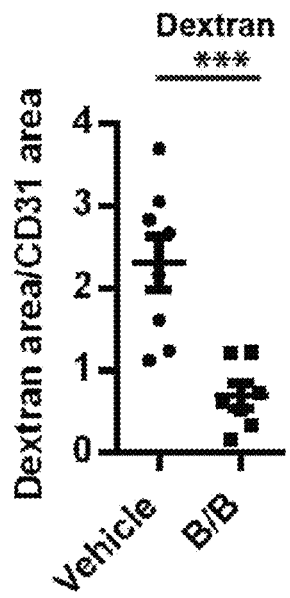
Figure 2L:
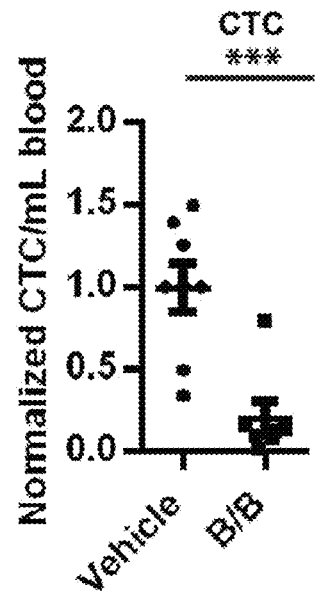
Figure 2M:
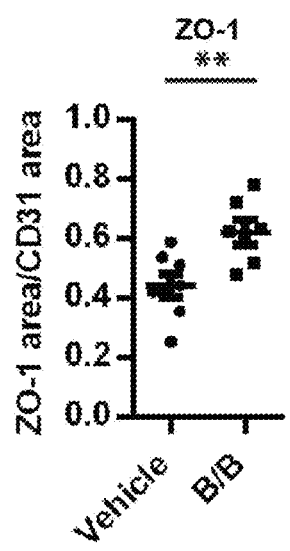
Figure 2N:
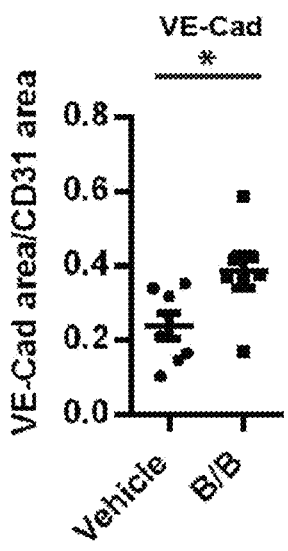

TMEM-associated macrophages are essential for vascular permeability and tumor cell intravasation. To determine if TMEM macrophages regulate vascular permeability and tumor cell intravasation, macrophages were depleted in the mammary tumor using the previously characterized mouse model, MAFIA (macrophage fas-induced apoptosis) (18, 19) with orthotopic MMTV-PyMT tumor implants. Depletion of macrophages is systemic, including the mammary tumor, thus resulting in a depletion of TAM and TMEM by 67% and 72% respectively (FIG. 2G-I). When macrophages are depleted, extravascular dextran decreases, as does the number of circulating tumor cells (FIGS. 2J, K and L). These data demonstrate that macrophages are essential for vascular permeability and tumor cell intravasation at TMEM.

Since blood vessel permeability observed by IVM is restricted to TMEM, it was examined if vascular junction protein localization was altered in the absence of macrophages, reflecting a requirement for macrophage-dependent signaling events to induce vascular permeability. Staining for vascular junction proteins ZO-1 and VE-Cadherin increased in the tumor vasculature after depletion of macrophages in MAFIA mouse tumors (FIGS. 2J, M and N) indicating that macrophages are involved in vascular junction disassembly during vascular permeability events at TMEM.

Figure 3A:
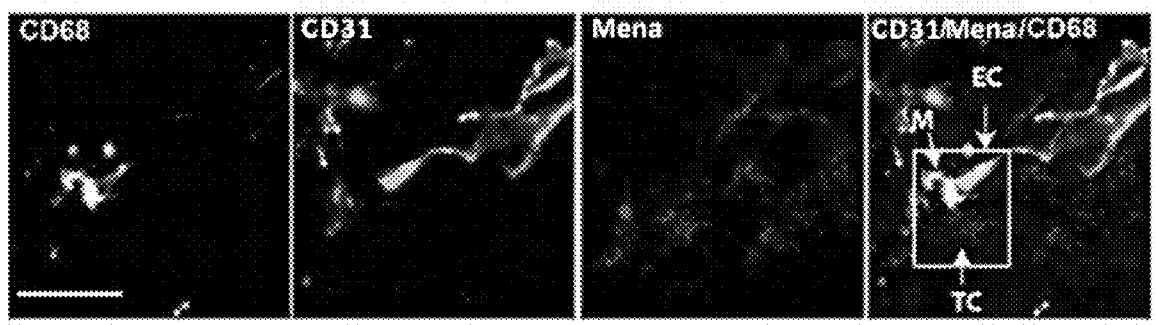
FIG. 3A-3K. Inhibition of VEGFA from Tie2$^{Hi}$/VEGF$^{Hi}$ TMEM macrophages reduces blood vessel permeability and tumor cell intravasation. (A) Immunofluorescence imaging of TMEM. Macrophages (CD68), blood vessels (CD31), tumor cells (Mena), and DAPI. TMEM in white box (right panel). Scale bar, 15 µm. (B) Immunofluorescence imaging of VEGFA$^{Hi}$ macrophages in TMEM in sequential sections. Scale bar, 10 µm. Tumor cell, spotted line; macrophages, solid line; and blood vessels, dashed line. Left panel: Macrophages (CD68), tumor cells (Mena), blood vessels (CD31), and DAPI. Sequential section (center panel): VEGFA, Tie2, blood vessels (CD31), and DAPI. Schematic representation (right panel) of protein expression in TMEM; tumor cells with Mena$^{Hi}$, endothelial cells CD31 and macrophages CD68, VEGFA$^{Hi}$ and Tie2$^{Hi}$. M, macrophage; TC, tumor cell; and EC, endothelial cell. (C) Immunofluorescence images of Tie2, VEGF and CD31. Lines indicate regions of intensity profiling of VEGF intensity for CD31 (EC), macrophage (M) and tumor tissue (TC). Scale bar, 25 µm. (D) Fluorescence intensity profile of VEGF from (C) of macrophage, endothelial cell and tumor tissue. (E) Immunofluorescence imaging of sequential PyMT tumor sections for TEM markers. VEGFA$^{Hi}$ TMEM macrophages express F4/80, MRC1, CD11b and CD68 as indicated by an arrowhead in sequential sections. CD31+ endothelium is indicated by an arrowhead. (F) VEGFA$^{Hi}$ TMEM macrophages express Tie2, MRC1, and CD68 but not CD11c as indicated by an arrowhead. CD31+/Tie2+ endothelium is indicated by an arrowhead. Scale bar, 25 µm. (G) Immunfluorescence imaging of tumor sections after blocking VEGFA with anti-VEGFA blocking antibody (B20-4.1.1). Tumors are stained for vasculature (CD31), 155 kDa dextran-TMR and DAPI, ZO-1 or VE-Cadherin as indicated. Scale bar, 50 µm. (H) Quantification of extravascular 155 kDa dextran-TMR and (n=10; **, P=0.0015) (I) circulating tumor cells (*, P=0.0497), (J) Vascular ZO-1 (**, P=0.005) and (K) Vascular VE-Cadherin (*, P=0.0463).
Figure 3B:
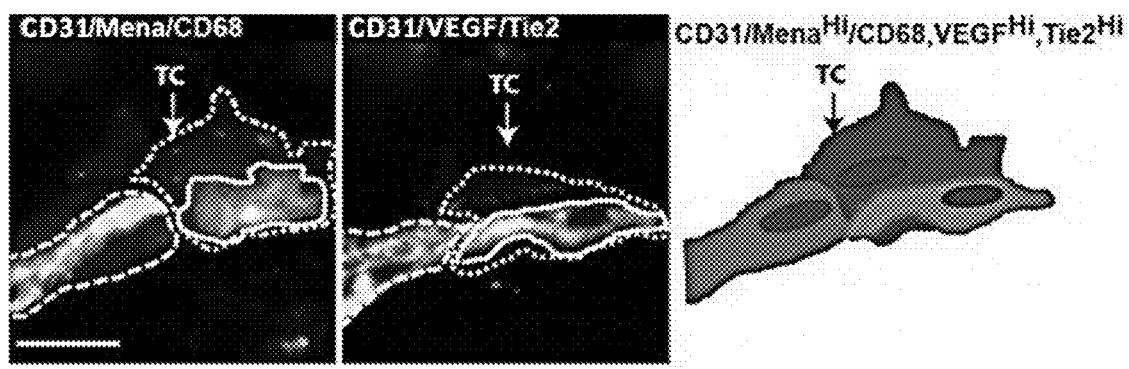
Figure 3C:
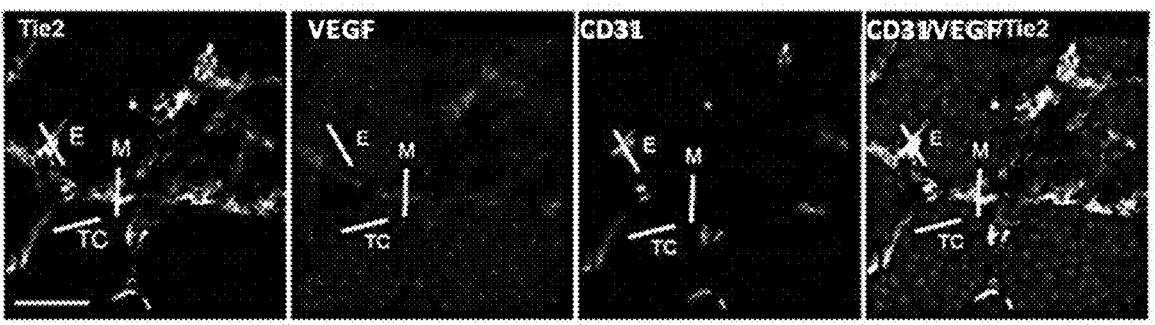
Figure 3D:
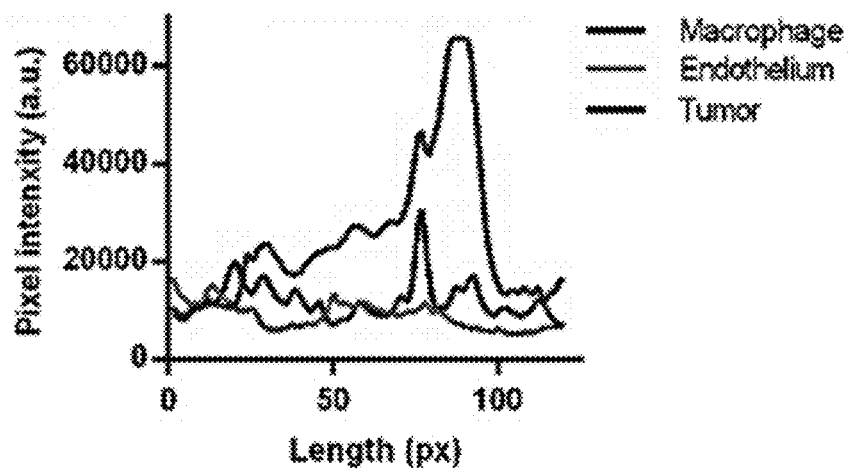
Figure 3E:
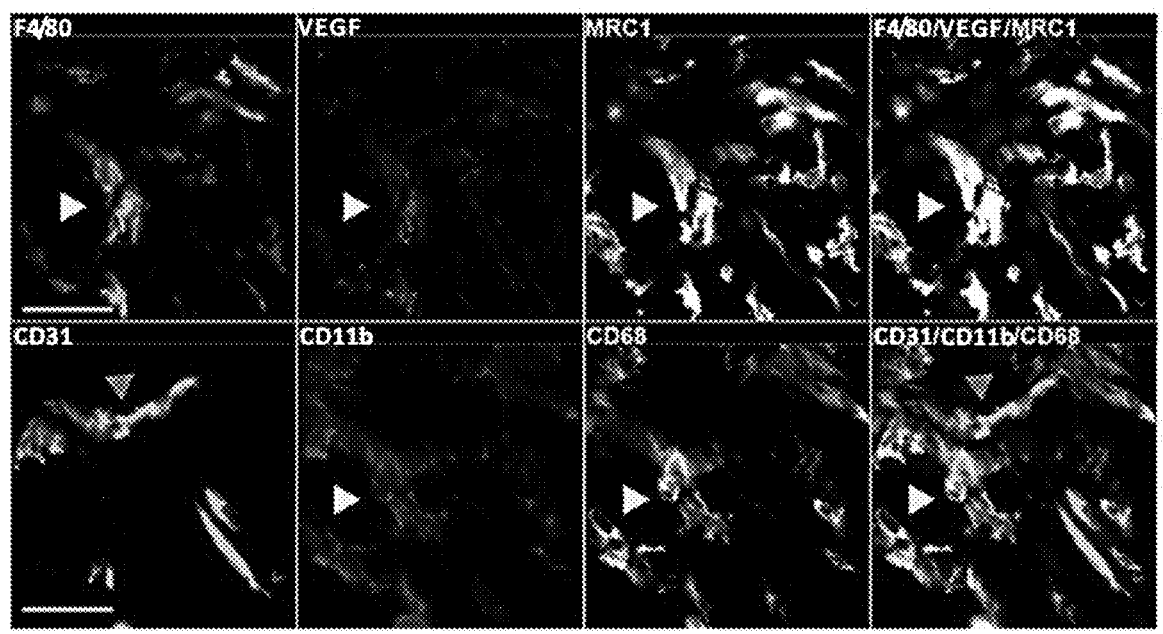
Figure 3F:
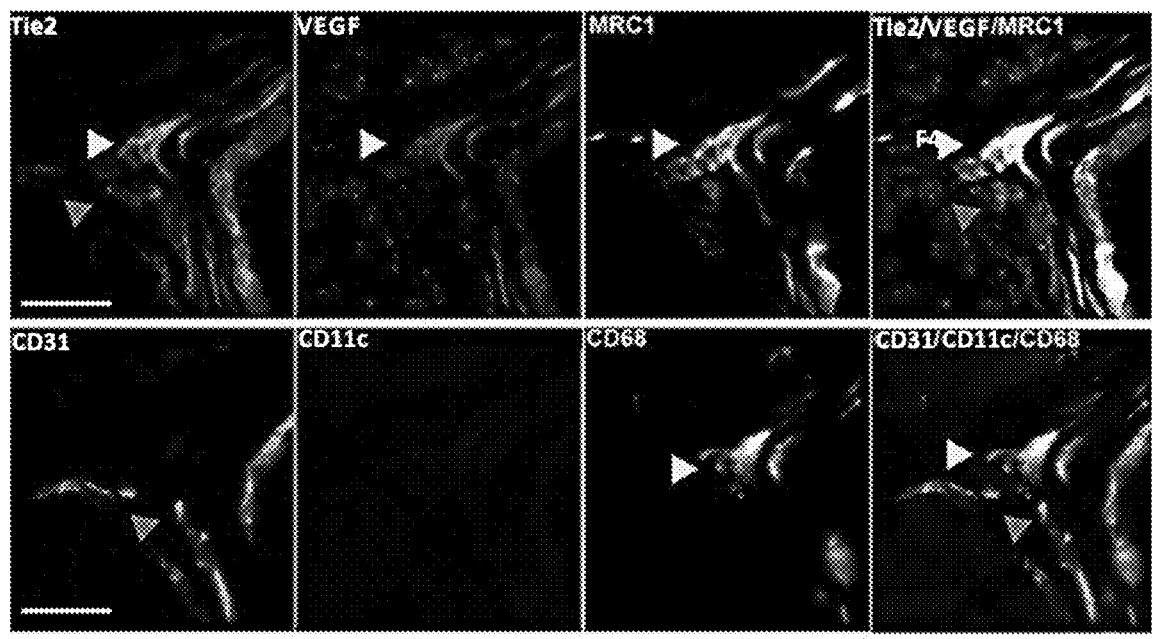

Tie2-expressing macrophages are localized in TMEM structures. In PyMT mammary carcinoma, a subpopulation of TAMs has been identified as $Tie2^{Hi}$ perivascular macrophages (7, 20, 21). Tie2-expressing macrophages (TEMs) have been shown to upregulate the Tie2 tyrosine kinase receptor by 100 fold after recruitment to the tumor (22). TEMs have features of pro-tumorigenic macrophages and promote tumor angiogenesis (7). TEMs are further characterized as MRC1+/CD11b+/F4/80+/CD11c− and are associated with CD31+ tumor blood vessels (20). Thus, it was determined if Tie2-expressing macrophages are located in TMEM. Immunofluorescence of TMEM markers Mena (tumor cells), CD31 (endothelial cells) and CD68 (macrophage) (FIG. 3A) compared to Tie2, VEGFA and CD31 in sequential tissue sections demonstrates that $Tie2^{Hi}$/$VEGFA^{Hi}$ macrophages are enriched in TMEM structures (FIG. 3B). VEGFA is elevated in $Tie2^{Hi}$ macrophages, as compared to the adjacent endothelial cells and surrounding tumor tissue (FIGS. 3C and D). Further, 100% of $Tie2^{Hi}$/$VEGFA^{Hi}$ TMEM-associated macrophages express the TEM markers MRC1, CD11b and F4/80 while lacking CD11c (FIG. 3E, F).

Figure 3G:
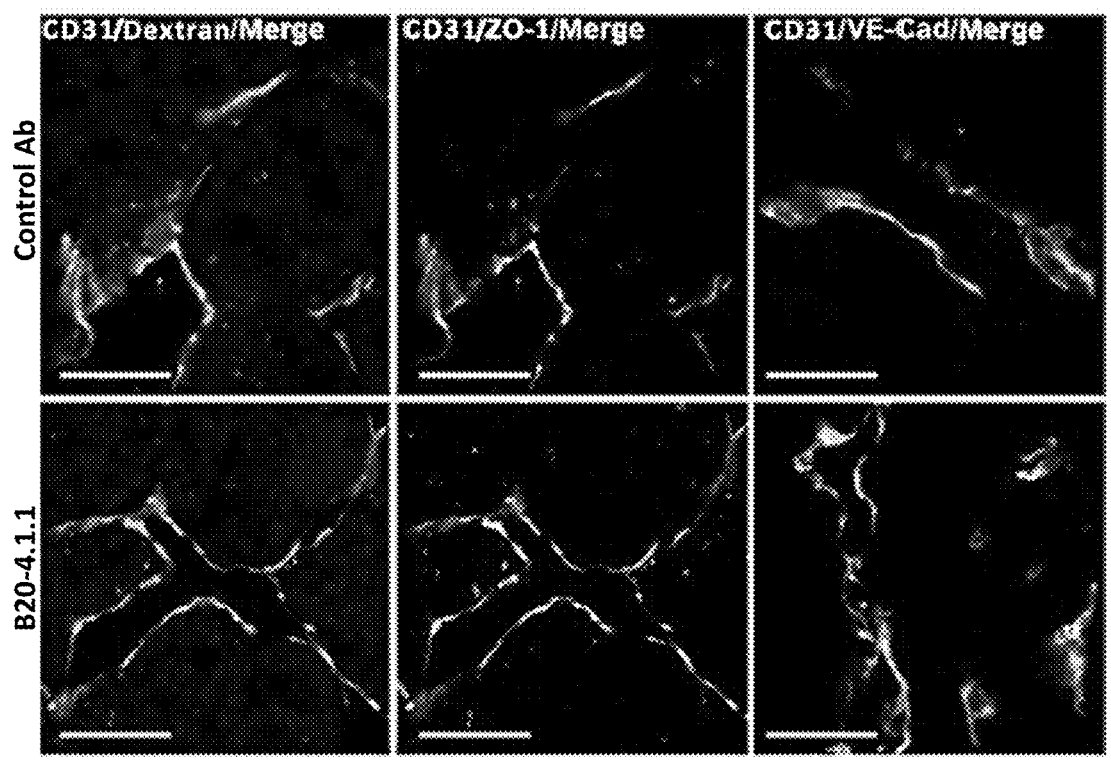
Figures 3H, 3I:
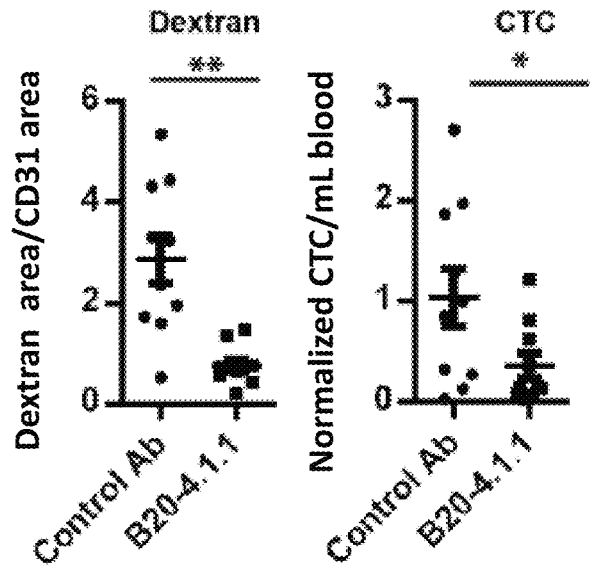
Figures 3J, 3K:
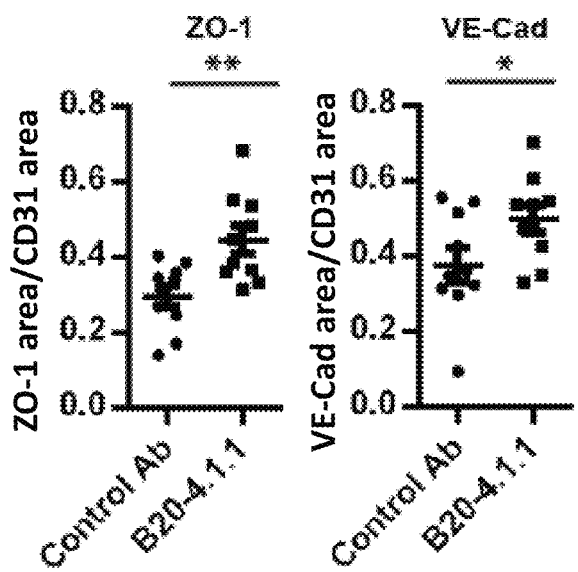

Inhibition of VEGFA signaling reduces vascular permeability and tumor cell intravasation. To investigate the importance of VEGFA in TMEM function, VEGFA binding to VEGF receptors was blocked using a neutralizing antibody (B20-4.1.1), which resulted in a decrease in extravascular dextran and circulating tumor cells (FIGS. 3G, H and I). Binding of VEGFA to VEGR2 leads to junction disassembly (23). Vascular ZO-1 and VE-Cadherin staining increased during VEGFA inhibition suggesting an increase in integrity of endothelial adherens and tight junctions from reduced bioavailability of VEGFA, including VEGFA from TMEM (FIGS. 3G, J and K).

Figure 4A:
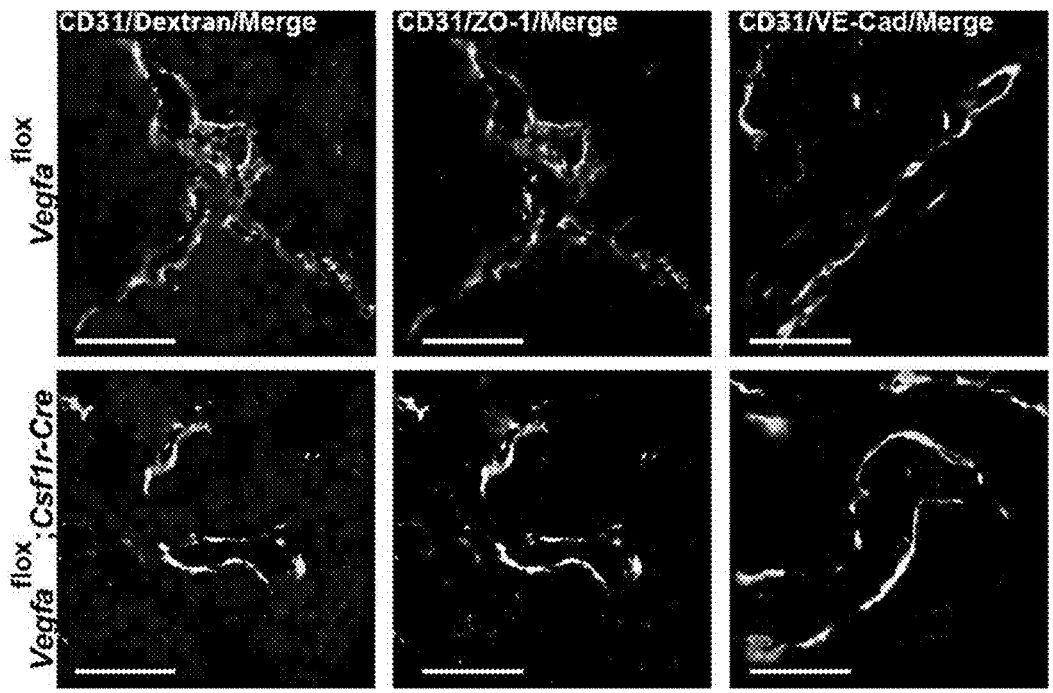
FIG. 4A-4M. Macrophage-specific ablation of Vegfa in PyMT implant tumors (Vegfa$^{flox}$; Csf1r-Cre) compared to control (Vegfa$^{flox}$) blocks blood vessel permeability and tumor cell intravasation. (A) Immunfluorescence of tumor sections stained for vasculature (CD31), 155 kDa dextran-TMR and DAPI, ZO-1 or VE-Cadherin as indicated. Scale bar, 50 µm. (B) Quantification of extravascular 155 kDa dextran-TMR and (Vegfa$^{flox}$ n=5, Vegfa$^{flox}$;Csf1r-Cre n=3; **; P=0.0029) (C) circulating tumor cells (*, P=0.0177) (D) Vascular ZO-1 (**, P=0.0054) and (E) Vascular VE-Cadherin (*, P=0.0457). (F, H) Immunofluorescence of tumor sections stained for the presence of vascular junction proteins at TMEM macrophages. Tumor sections are stained for VE-cadherin, CD31 and VEGFA. Sequential sections are stained for CD31, Tie2 and CD68. (F) Control tumors (Vegfa$^{flox}$) or (H) after ablation of Vefga (Vegfa$^{flox}$;Csf1r-Cre). CD68+ macrophage in TMEM outlined in white box, adjacent endothelium in TMEM in box. Merged signal of CD31 and Tie2 (left) or CD31 and VE-Cadherin (right). Decreased VE-Cadherin at TMEM (F, right) seen as decreased VE-Cadherin. Scale bar, 15 µm. (G, I) Quantification of the relative intensity of VEGFA or vascular junction proteins (ratio of VE-cadherin to CD31 in blood vessels) in F, H at TMEM or away from TMEM in (G) control tumors (Vegfa$^{flox}$) or (I) after ablation of Vegfa in Vegfa$^{flox}$; Csf1r-Cre tumors along 25 µm lengths of blood vessel (n=3). (●) Relative fluorescence intensity of VE-Cadherin/CD31, (■) Relative VEGFA intensity. Dashed line indicates the presence of a CD68+ macrophage. (J) Quantification of average pixel intensity of VE-Cadherin/CD31 immunofluorescence staining in 25 µm lengths of blood vessel at TMEM or away from TMEM in the presence of VEGFA$^{Hi}$ macrophages (Vegfa$^{flox}$, n=3) or after macrophage-specific ablation of Vegfa (Vegfa$^{flox}$;Csf1r-Cre, n=3) from data in G and I. Post-ANOVA comparisons with significant difference indicated (*, ). (K) Cartoon summarizing TMEM macrophage-mediated induction of blood vessel permeability promotes tumor cell intravasation. TMEM assemble with close association between the non-migratoryTMEM TC (T1) and Tie2$^{Hi}$/VEGFA$^{Hi}$ macrophage (bM1) on blood vessels. VEGFA destabilizes vascular junctions resulting in vascular permeability and TC (T2) intravasation. (L) Human breast cancer tumor sections stained for the presence of vascular junction proteins at TMEM macrophages. Tumor sections are stained for TMEM; Mean, CD68 and CD31 by IHC and for VE-cadherin, Tie2 and VEGFA stained by immunofluorescence in sequential sections. TMEM outlined in black box in IHC and white box in immunofluorescence. Scale bar, 15 µm. (M) Quantification of normalized average pixel intensity of VE-Cadherin staining in vasculature at Tie2Hi/VEGFAHi macrophages of TMEM or away from TMEM in (n=23 at TMEM, n=24 away from TMEM in 5 individual patient samples, *, P=0.0001).
Figures 4B, 4C:
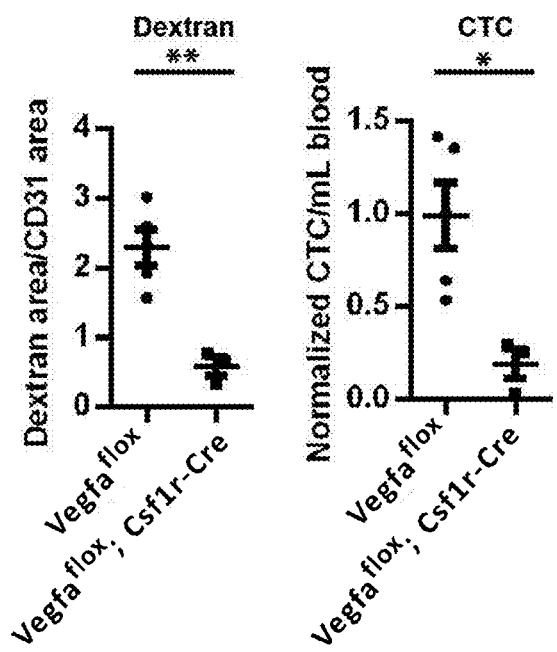
Figure 4D:
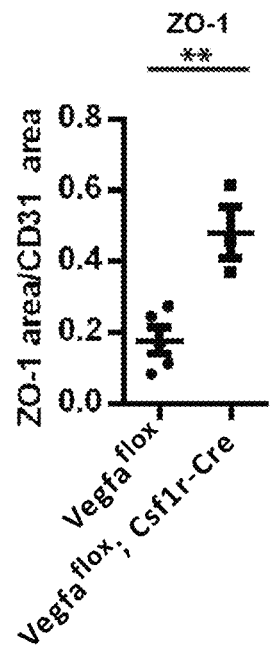
Figure 4E:
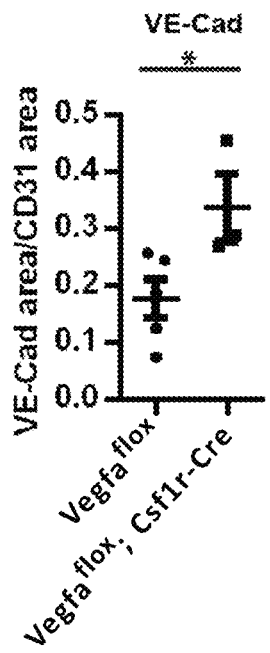
Figure 4F:
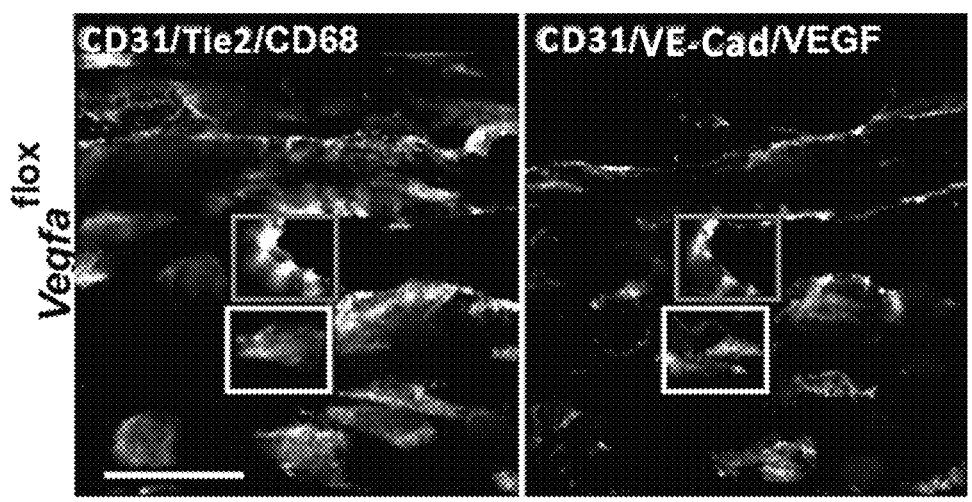
Figure 4G:
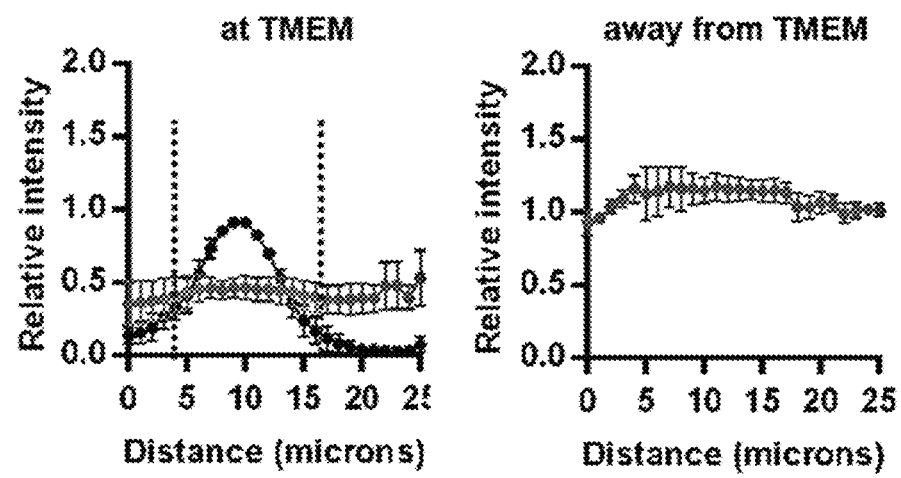
Figure 4H:
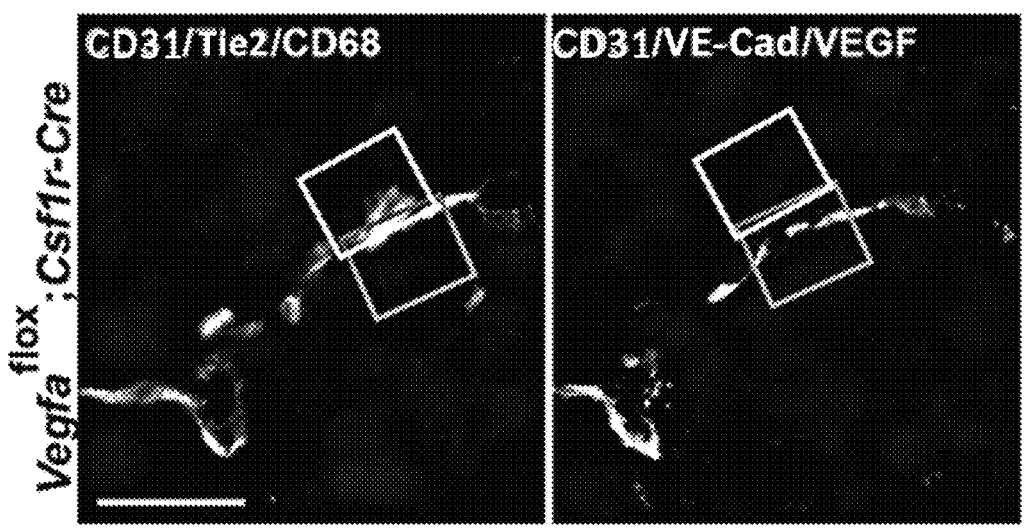
Figure 4I:
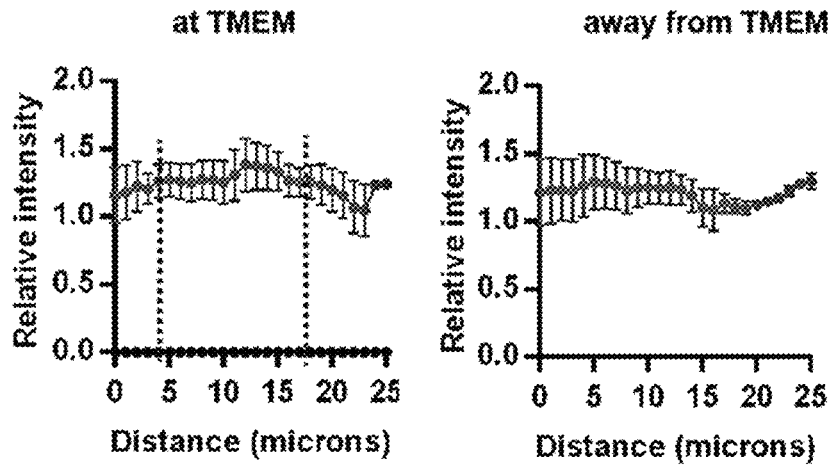
Figure 4J:
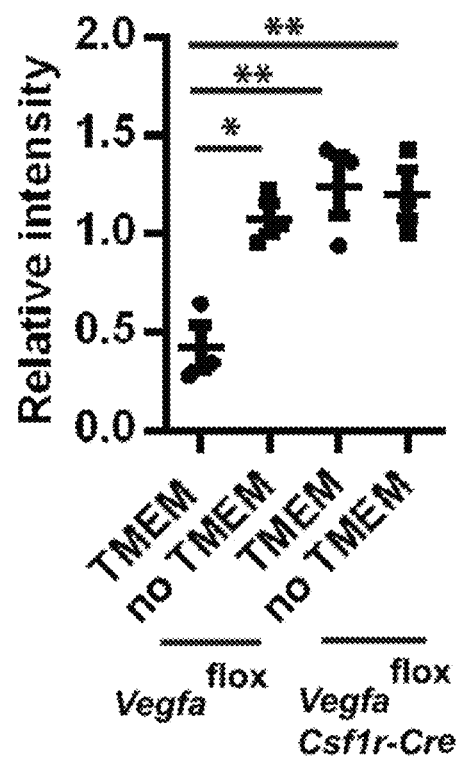

VEGFA signaling from $Tie2^{Hi}$/$VEGFA^{Hi}$ TMEM macrophages mediates vascular permeability and tumor cell intravasation. To determine if the subpopulation of $Tie2^{Hi}$/$VEGFA^{Hi}$ macrophages in TMEM are an essential source of VEGFA in the tumor microenvironment required for transient vascular permeability at TMEM and tumor cell intravasation, VEGFA was selectively ablated in monocytes and macrophages using the Vegfaflox/flox; Csf1r-Mer-iCre-Mer transgenic mouse depletion model of Vegfa that targets myeloid cells expressing Csf1r, including both $Ly6C^{Hi}$ and $Ly6C^{Lo}$ populations, including the TEM population (24). Macrophage-specific depletion of VEGFA reduced transient vascular permeability, and circulating tumor cells, while restoring vascular junctions (FIGS. 4A, B, C, D and E). Immunofluorescence of sequential sections demonstrates that blood vessels adjacent to CD68+/$Tie2^{Hi}$/$VEGFA^{Hi}$ TMEM macrophage have significantly reduced vascular VE-Cadherin/CD31 relative intensity compared to regions of vasculature away from TMEM sites in $Vegfa^{flox}$ tumors (FIGS. 4 F and G). Further, when VEGFA has been ablated in $Vegfa^{flox}$; Csf1r-Cre tumors VE-Cadherin/CD31 relative staining intensity is the same along the tumor vasculature as in regions away from TMEM (FIGS. 4H and I). Therefore, vascular junction integrity, as measured by VE-Cadherin/CD31 relative staining intensity, is only significantly reduced in regions of vasculature adjacent to $VEGFA^{Hi}$ TMEM macrophages in TMEM (FIG. 4J). Further, pericyte coverage of the vasculature is reduced in regions of $VEGFA^{Hi}$ TEMs in TMEM as compared to regions away from $VEGFA^{Hi}$ TMEM structures. A decrease in pericyte coverage of vasculature has been correlated with increased metastasis and vascular permeability (25).

Figure 4K:
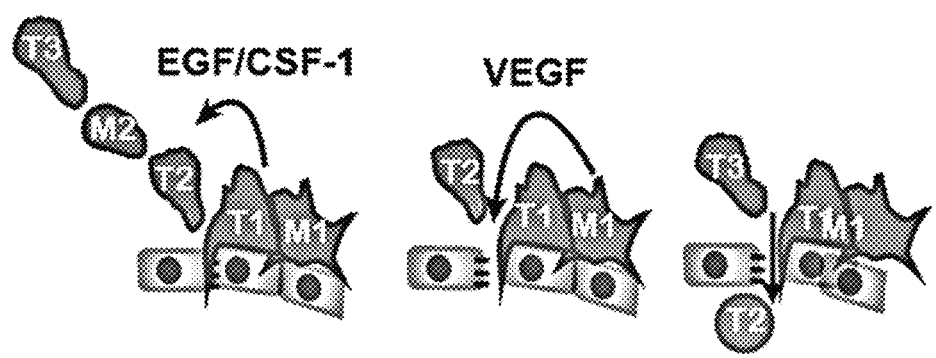
Figure 4L:
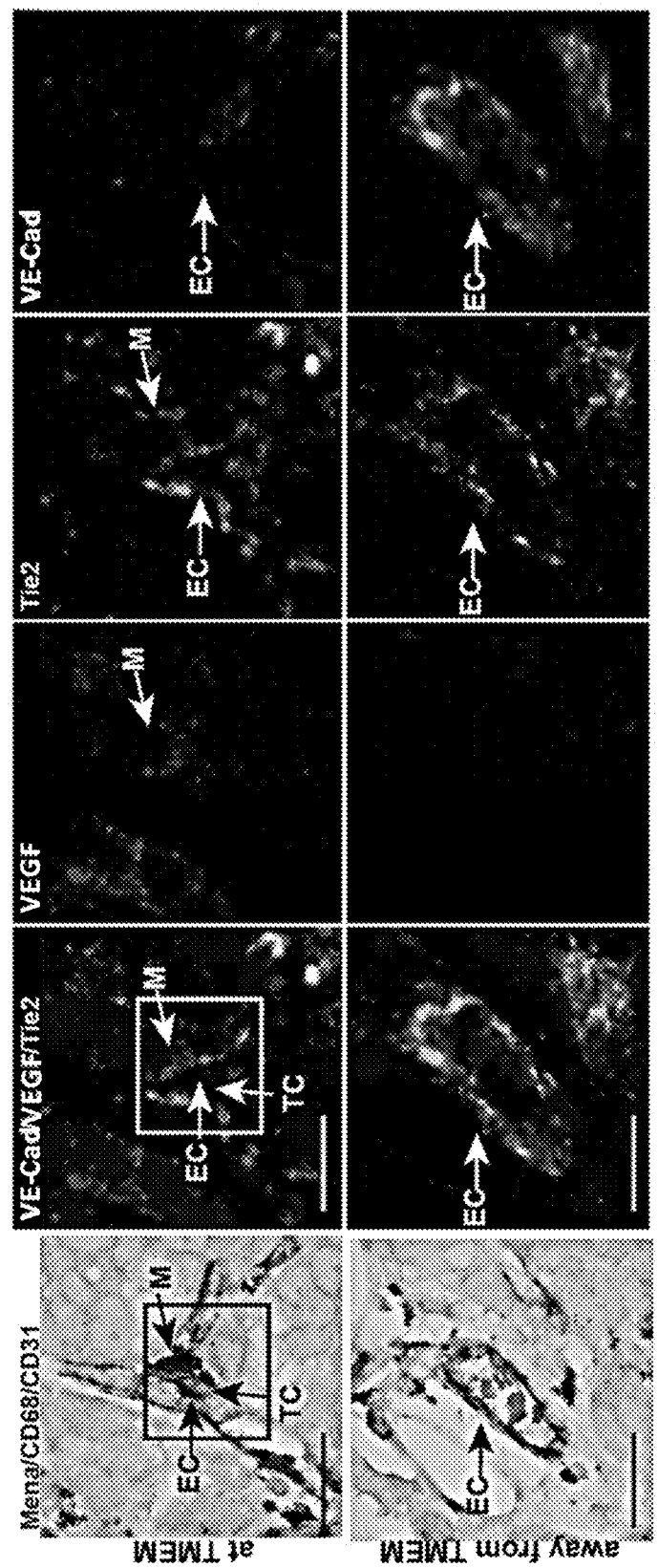
Figure 4M:
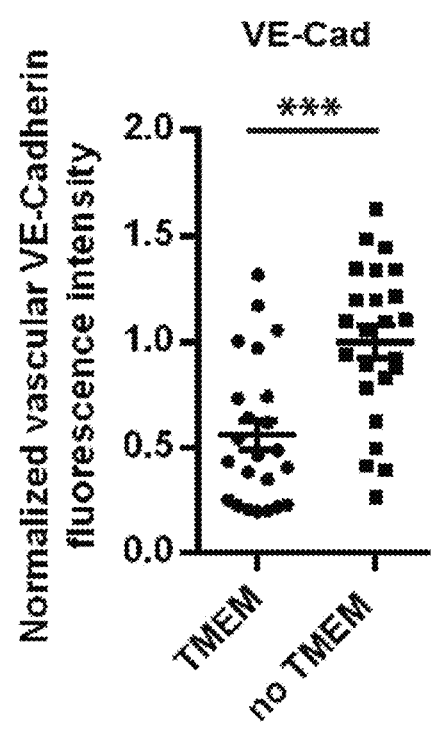
Figure 5A:
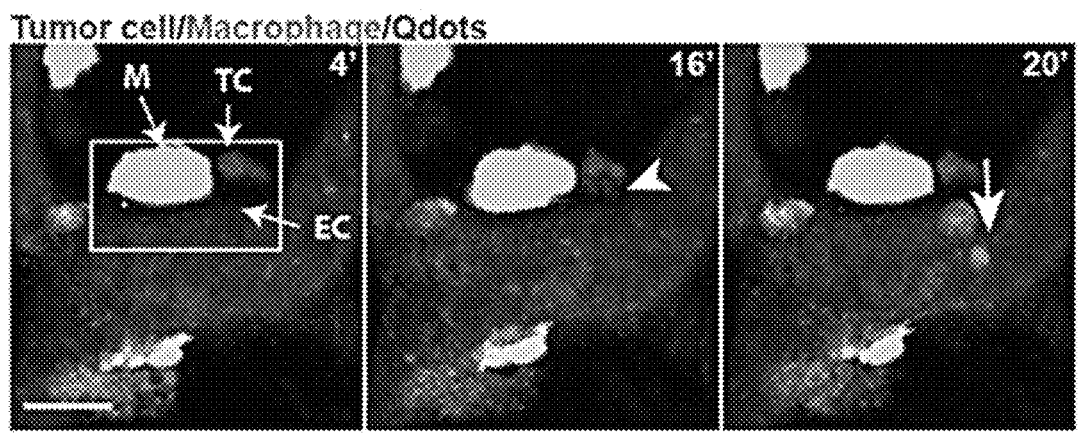
Figure 5B:
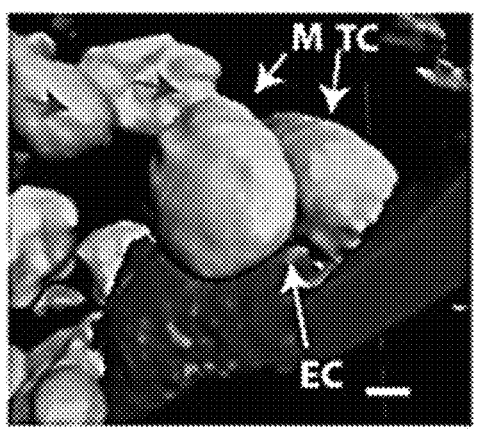
Figure 5G:
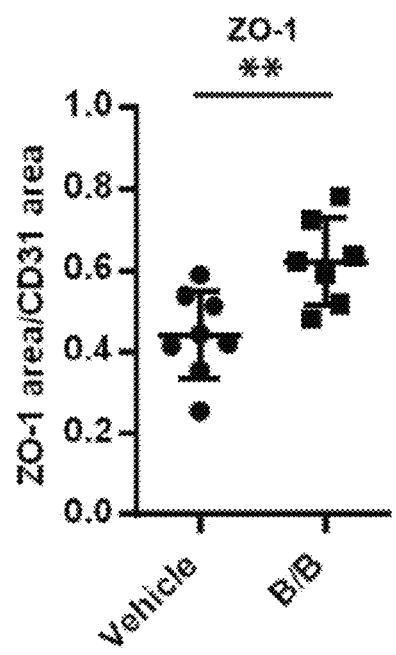
Figure 5H:
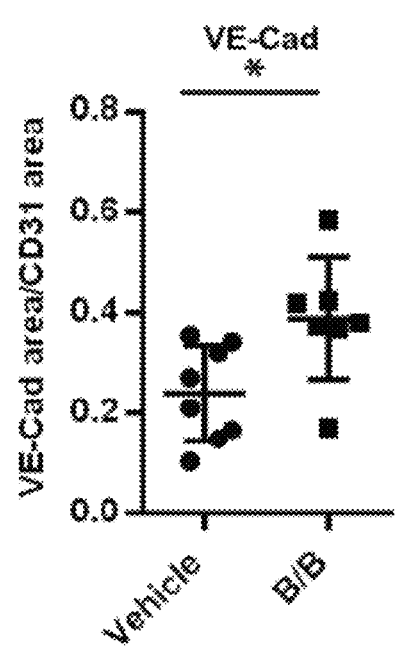

To establish the relevance of $Tie2^{Hi}$/$VEGFA^{Hi}$ macrophages in TMEM structures in mediating vascular permeability and tumor cell dissemination in metastastic breast cancer, vascular junction staining was measured in human breast cancer patient samples. Staining of sequential sections demonstrates that blood vessels adjacent to $Tie2^{Hi}/VEGFA^{Hi}$ macrophages in TMEM have significantly reduced vascular VE-Cadherin fluorescence intensity compared to regions of vasculature away from TMEM (FIG. 4L, M).

Together these data establish that the $Tie2^{Hi}/VEGFA^{Hi}$ TMEM macrophages interact with endothelial cells through VEGFA signaling to mediate local, transient blood vessel permeability demonstrating the mechanism underlying the clinically-demonstrated association of TMEM density with metastatic recurrence of breast cancer.

Discussion

Although the abnormality and permeability of tumor vasculature has been well characterized, the mechanism leading to spatial and temporal heterogeneity in permeability has not been resolved. The use of high-resolution multiphoton microscopy has allowed for the study of vascular permeability and tumor cell dissemination in mammary carcinoma at unprecedented spatial and temporal resolution. The present data show that in the PyMT authochthonous mouse mammary carcinoma and human patient-derived xenograft TN1 models, that vascular permeability is dynamic, localized, and restricted to TMEM. These data are consistent with previous findings that hyperpermeability of tumor vasculature is heterogeneous and often in the presence of perivascular macrophages (4), but further explains the observed heterogeneity and that tumor cell intravasation occurs at sites of vascular permeability.

The sites of dynamic tumor vascular permeability have been identified at sites of $VEGFA^{Hi}$ perivascular macrophages at TMEM. The clinical significance of TMEM density in predicting metastatic risk has been recently expanded to a large cohort of patients, further emphasizing the importance of TMEM in breast cancer metastasis (26). These data demonstrate that $Tie2^{Hi}/VEGFA^{Hi}$ perivascular macrophages in TMEM share the characteristics of the pro-angiogenic and pro-metastatic Tie2-expressing macrophages (7).

Mechanistically, macrophage/tumor cell streams migrate to TMEM sites through the EGFR/CSF-1R paracrine loop (27). Elevated expression of VEGFA in the $Tie2^{Hi}$ TMEM macrophage results in transient permeability of tumor blood vessels proximal to TMEM that occurs by disassembling endothelial cell junctions. The simultaneous attraction of migratory tumor cells and transient blood vessel permeability results in a concurrent spike in tumor cell intravasation with vascular permeability at TMEM sites (FIG. 4K). These data, together with the clinical association of TMEM with distant metastatic tumor recurrence in human breast cancer patients explain why TMEM density can predict metastasis and argues for the development of therapeutic approaches targeted against both TMEM formation and function.

$TMEM^{ACTIVE}$ Test

Figure 9A:
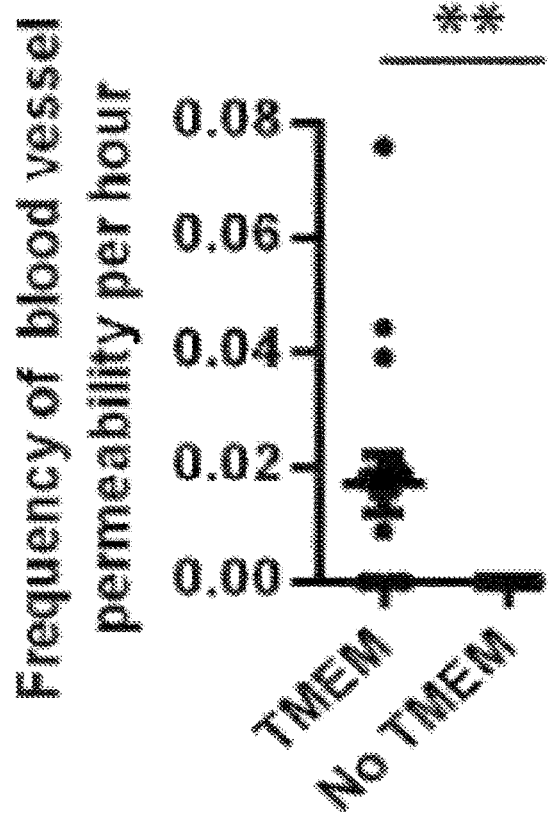
FIG. 9A-9B. Blood vessel permeability and tumor cell intravasation are linked and occur only at TMEM sites. (A) Frequency of blood vessel permeability events in the presence of TMEM or away from TMEM (n=16, , P=0.0034). (B) Frequency of tumor cell intravasation events in the presence of TMEM or away from TMEM (n=16, , P=0.0012).
Figure 9B:
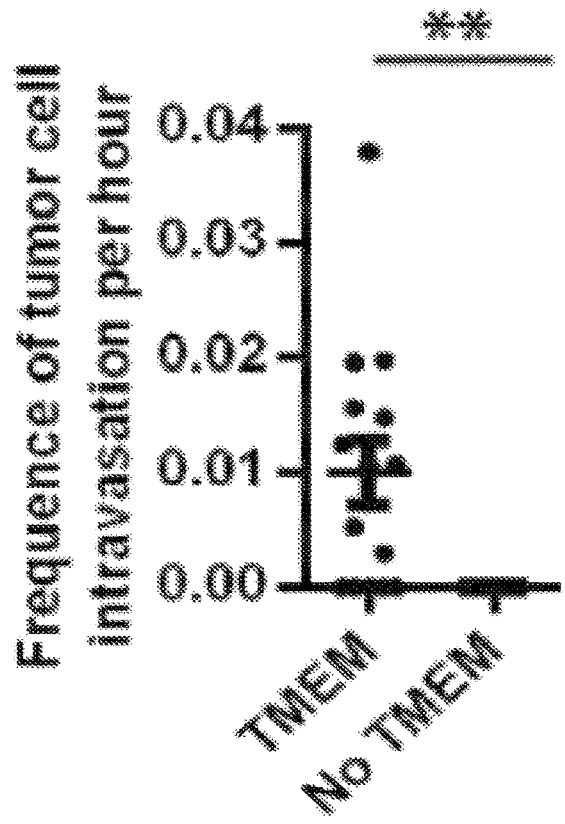

Hematogenous dissemination of tumor cells from the primary tumor is an essential step in metastasis and is unrelated to growth potential. The sites of tumor cell dissemination are called TMEM which is defined as the direct contact between a macrophage, tumor cell and endothelial cell (9, 28). The sum of TMEM number in ten 40× fields predicts the risk of distant recurrence in breast cancer patients (11, 28). Intravital high-resolution two-photon microscopy of live mammary tumors shows that vascular leakiness and tumor cell intravasation occur exclusively at TMEM (FIG. 5A-D). This, dissemination of tumor cells from solid tumors such as breast tumors occurs only at TMEM (FIG. 9A,B). Ablation of TMEM macrophages blocks TMEM-associated vascular leakiness and intravasation, demonstrating an essential role of macrophages in TMEM function (FIG. 5E-H).

Figure 6A:
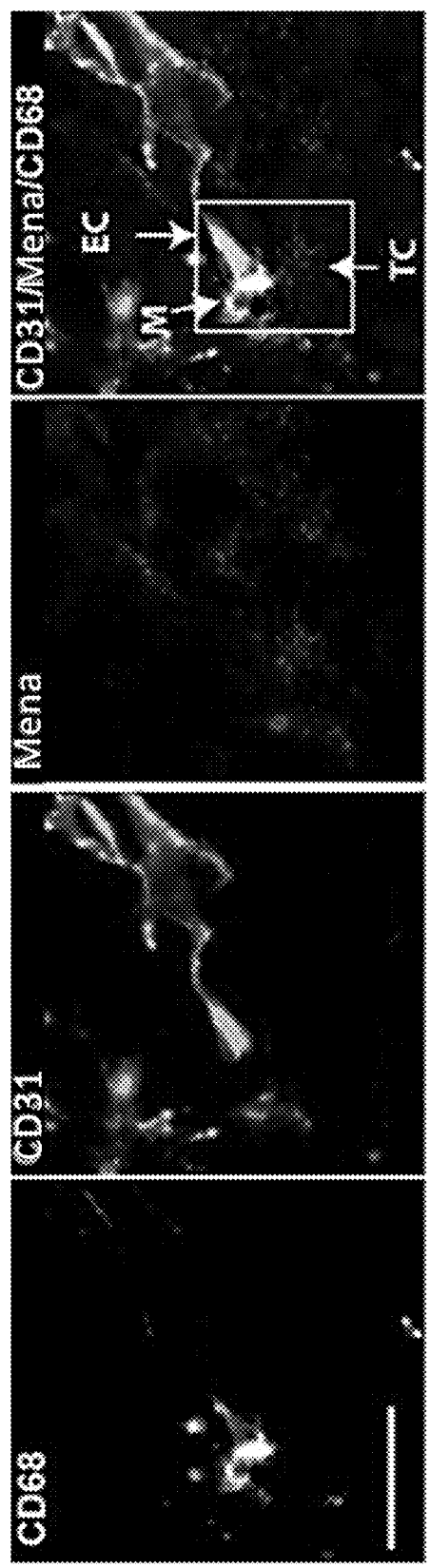
FIG. 6A-6B. TMEM macrophages are VEGF$^{Hi}$/Tie2$^{Hi}$/CD68+. (A) Immunofluorescence imaging of TMEM. Macrophages (CD68), blood vessels (CD31), tumor cells (Mena), and DAPI. TMEM in white box (right panel). (B) Immunofluorescence imaging of VEGF$^{Hi}$ macrophages in TMEM in sequential sections. Tumor cell, spotted line; macrophages, solid line; and blood vessels, dashed line. Left panel: Macrophages (CD68), tumor cells (Mena), blood vessels (CD31), and DAPI. Sequential section (center panel): VEGFA, Tie2, blood vessels (CD31), and DAPI. Schematic representation (right panel) of protein expression in TMEM; tumor cells with Mena$^{Hi}$, endothelial cells CD31 and macrophages CD68, VEGFA$^{Hi}$ and Tie2$^{Hi}$. M, macrophage; TC, tumor cell; and EC, endothelial cell.
Figure 6B:
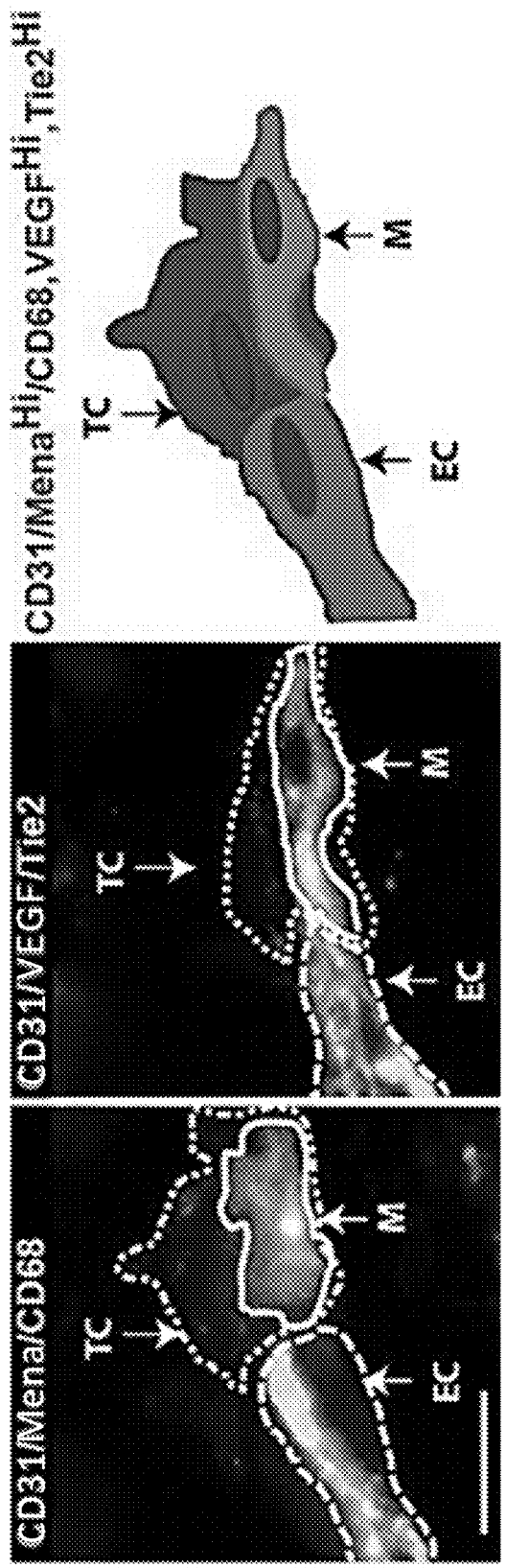

Macrophages in TMEM are $Tie2^{Hi}/VEGFA^{Hi}$ (FIG. 6). $Tie2^{Hi}/VEGFA^{Hi}$ peri-vascular macrophages are the type of macrophage that is found in TMEM. The presence of a $Tie2^{Hi}/VEGFA^{Hi}$ macrophage in contact with a blood vessel indicates a site of TMEM. TMEM can be identified as $Tie2^{Hi}/VEGFA^{Hi}$ CD68+ cells in direct contact with a blood vessel.

Figures 7A, 7B, 7C, 7D:
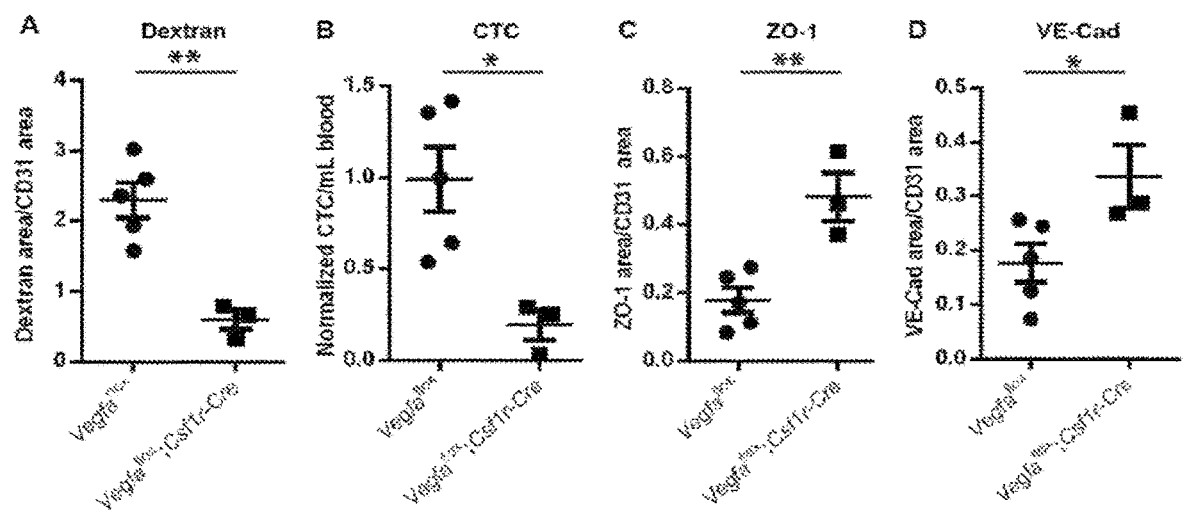
FIG. 7A-7D. Macrophage-specific ablation of Vegfa in PyMT implant tumors blocks blood vessel permeability and tumor cell intravasation. Quantification in the presence (Vegfa$^{flox}$ n=5) or absence (Vegfa$^{flox}$;Csf1r-Cre n=3) of Vegfa in macrophages of (A) extravascular 155 kDa dextran-TMR in (**; P=0.0029) (B) circulating tumor cells (*, P=0.0177) (C) Vascular ZO-1 (**, P=0.0054) and (D) Vascular VE-Cadherin (*, P=0.0457).

VEGFA signaling from $Tie2^{Hi}/VEGFA^{Hi}$ TMEM-associated macrophages causes local loss of vascular endothelial cell junctions (ZO-1 and VE-Cadherin decrease), resulting in transient endothelial permeability and tumor cell intravasation (FIG. 7). This discovery demonstrates a way to assess the activity status of TMEM in disseminating tumor cells and to investigate the efficacy of drug intervention in vascular leakiness and associated tumor cell intravasation (FIG. 8).

Hence, the simultaneous staining of Tie2, VEGFA, CD68, CD31 and VE-Cadherin and/or ZO-1 in (e.g., Formalin-Fixed, Paraffin-Embedded (FFPE)) tumor tissue provides a test to assess the activity status of TMEM ($TMEM^{Active}$) in a patient and the efficacy of dissemination inhibitor drugs that inhibit TMEM activity. $Tie2^{Hi}/VEGFA^{Hi}$ peri-vascular macrophages associated with low levels of VE-Cadherin and ZO-1 endothelial staining indicate TMEM sites that are active in tumor cell dissemination while $Tie2^{Hi}/VEGFA^{Hi}$ peri-vascular macrophages associated with high levels of VE-Cadherin and ZO-1 endothelial staining indicate TMEM sites that are inactive in tumor cell dissemination (FIGS. 5E-H, 7A-D and 8).

Figure 10:
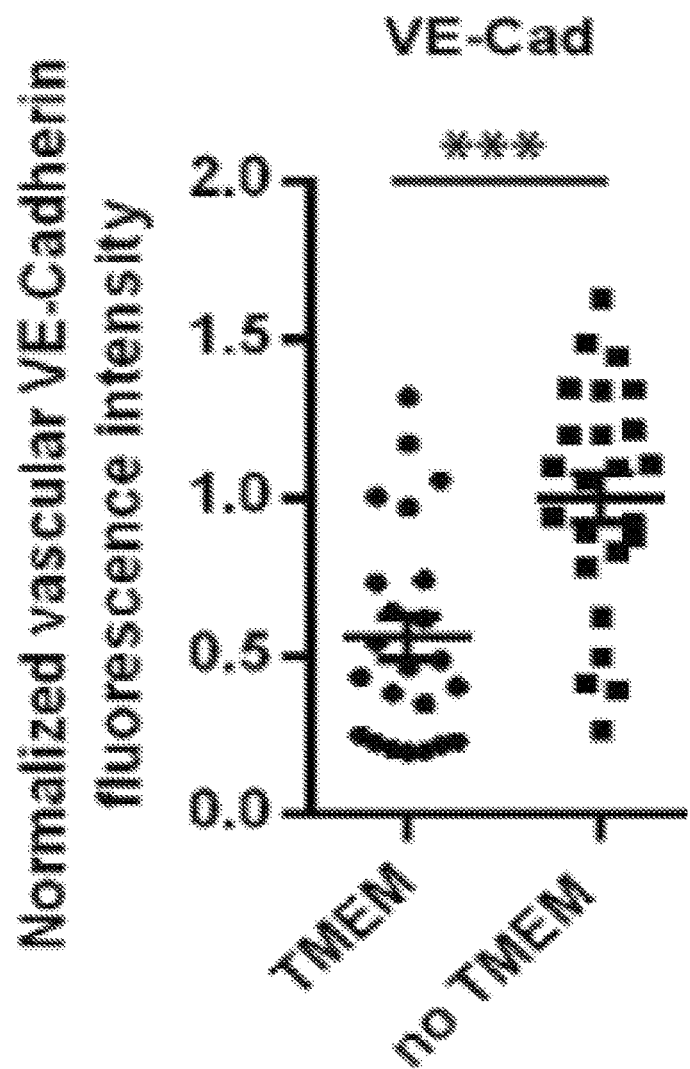
FIG. 10. Quantification of normalized average pixel intensity of VE-Cadherin staining in vasculature at Tie2$^{Hi}$/VEGFA$^{Hi}$ macrophages of TMEM or away from TMEM (n=23 at TMEM, n=24 away from TMEM) in 5 individual patient samples (***, P=0.0001).

When TMEM is active the endothelial cell junctions between blood vessel endothelial cells in contact with TMEM are disrupted leading to a loss of VE-Cadherin and ZO-1 endothelial staining, which is correlated with tumor cell intravasation and dissemination. When TMEM are inactive the level of VE-Cadherin and ZO-1 endothelial staining at TMEM will be higher than in active TMEM and identical to the level of staining observed in blood vessels that are not associated with TMEM in neighboring tissue (FIG. 10). Hence, the $TMEM^{Active}$ assay is inherently quantitative and always has an intrinsic control in the same tissue section (areas away from TMEM=no TMEM in FIG. 10).

Figure 12A:
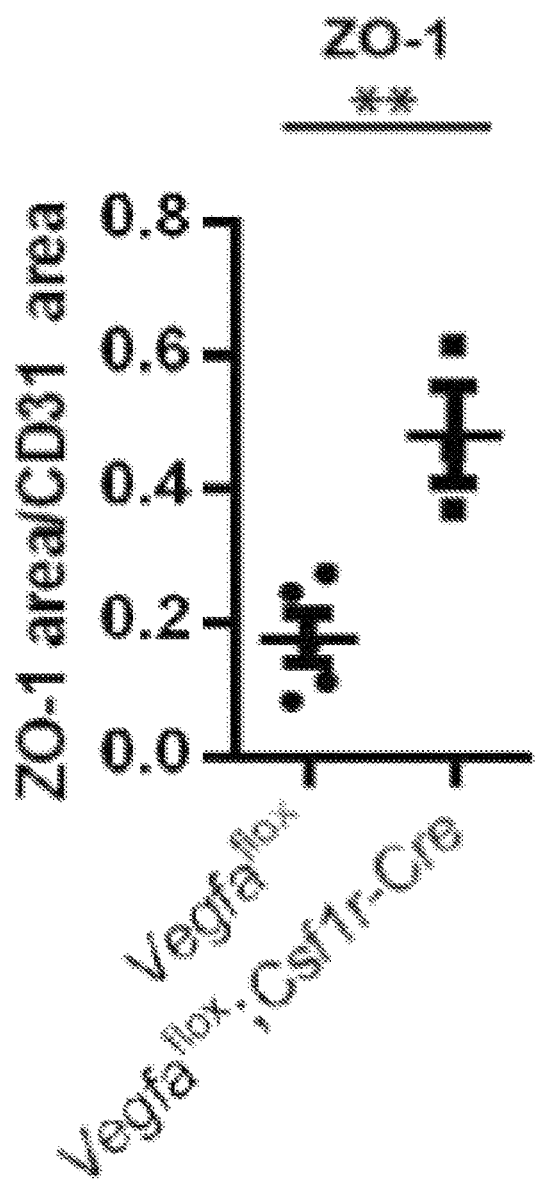
FIG. 12A-12B. Knockout of the VEGF gene (csf1-cre) in Tie2Hi macrophages blocks TMEM macrophage function. Quantification of (A) Vascular ZO-1 (**, P=0.0054) and (B) Vascular VE-Cadherin (*, P=0.0457), normalized to blood vessel area (ZO-1 or VE-Cad staining intensity/anti-CD31 staining intensity).
Figure 12B:
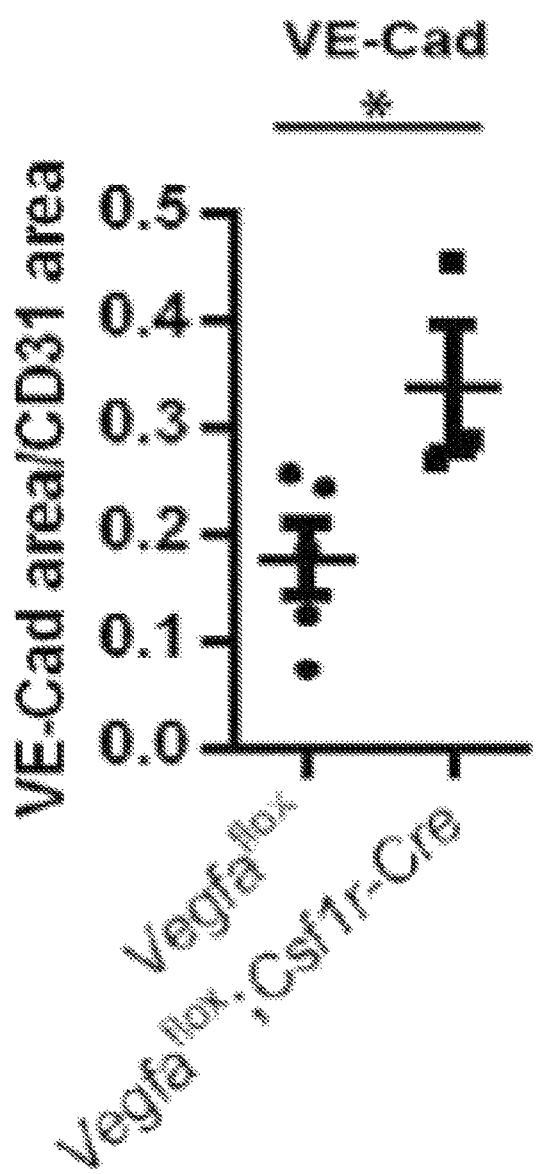

The relative activity of TMEM can be quantified in (e.g., FFPE) tissue sections in several ways, e.g.:
1. as the ratio of IV-dextran (or other IV contrast agent) that has leaked from the blood vessel into the tissue at the time of Formaldehyde Fixation after IV injection of contrast agent in preparation for FFPE (measure of local vascular permeability) divided by ZO-1 or VE-Cad staining intensity at TMEM (FIG. 11). Higher dextran/ZO-1=more TMEM activity;
2. as the ratio of ZO-1 or VE-Cad staining intensity at TMEM per area of blood vessel (CD31 staining area) (FIG. 12). Higher VE-Cad or ZO-1/CD31=less TMEM activity;
3. as the absolute intensity of ZO-1 or VE-Cad staining intensity at TMEM sites (FIG. 10). Higher VE-Cad staining=less TMEM activity.

The activity status of TMEM ($TMEM^{Active}$) in patient tissue samples can be used to assess the efficacy of dissemination inhibitor drugs that inhibit TMEM activity. For example, observe the effects of the following dissemination inhibitors on $TMEM^{Active}$ using the quantitation methods for TMEM activity described in #1-3 above as follows:

a. Rebastinib, the Tie2 inhibitor which blocks VEGF$^{Hi}$ TMEM macrophage function, (FIG. 11);
b. Knockout of the VEGF gene (Csf1r-cre) in macrophages which blocks TMEM macrophage function (FIG. 12).

REFERENCES

1. Yuan F, Dellian M, Fukumura D, Leunig M, Berk D A, Torchilin V P, et al. Vascular permeability in a human tumor xenograft: molecular size dependence and cutoff size. Cancer Res. 1995; 55:3752-6.
2. Gerlowski L E, Jain R K. Microvascular permeability of normal and neoplastic tissues. Microvasc Res. 1986; 31:288-305.
3. Huang Y, Goel S, Duda D G, Fukumura D, Jain R K. Vascular Normalization as an Emerging Strategy to Enhance Cancer Immunotherapy. Cancer Research. 2013; 73:2943-8.
4. Dvorak H F, Orenstein N S, Carvalho A C, Churchill W H, Dvorak A M, Galli S J, et al. Induction of a fibrin-gel investment: an early event in line 10 hepatocarcinoma growth mediated by tumor-secreted products. J Immunol. 1979; 122:166-74.
5. Lin E Y, Nguyen A V, Russell R G, Pollard J W. Colony-stimulating factor 1 promotes progression of mammary tumors to malignancy. J Exp Med. 2001; 193:727-40.
6. Lin E Y, Li J F, Gnatovskiy L, Deng Y, Zhu L, Grzesik D A, et al. Macrophages regulate the angiogenic switch in a mouse model of breast cancer. Cancer Res. 2006; 66:11238-46.
7. De Palma M, Venneri M A, Galli R, Sergi L S, Politi L S, Sampaolesi M, et al. Tie2 identifies a hematopoietic lineage of proangiogenic monocytes required for tumor vessel formation and a mesenchymal population of pericyte progenitors. Cancer Cell. 2005; 8:211-26.
8. Robinson B D, Sica G L, Liu Y F, Rohan T E, Gertler F B, Condeelis J S, et al. Tumor microenvironment of metastasis in human breast carcinoma: a potential prognostic marker linked to hematogenous dissemination. Clin Cancer Res. 2009; 15:2433-41.
9. Roh-Johnson M, Bravo-Cordero J J, Patsialou A, Sharma V P, Guo P, Liu H, et al. Macrophage contact induces RhoA GTPase signaling to trigger tumor cell intravasation. Oncogene. 2014 Aug. 14; 33(33):4203-12. Epub 2013 Sep. 23.
10. Wyckoff J B, Wang Y, Lin E Y, Li J F, Goswami S, Stanley E R, et al. Direct visualization of macrophage-assisted tumor cell intravasation in mammary tumors. Cancer Res. 2007; 67:2649-56.
11. Rohan T E, Xue X, Lin H-M, D'Alfonso T M, Ginter P S, Oktay M H, et al. Tumor Microenvironment of Metastasis and Risk of Distant Metastasis of Breast Cancer. Journal of the National Cancer Institute. 2014; 106(8).
12. Monsky W L, Fukumura D, Gohongi T, Ancukiewcz M, Weich H A, Torchilin V P, et al. Augmentation of transvascular transport of macromolecules and nanoparticles in tumors using vascular endothelial growth factor. Cancer Res. 1999; 59:4129-35.
13. Lin E Y, Jones J G, Li P, Zhu L, Whitney K D, Muller W J, et al. Progression to malignancy in the polyoma middle T oncoprotein mouse breast cancer model provides a reliable model for human diseases. Am J Pathol. 2003; 163:2113-26.
14. Dreher M R, Liu W, Michelich C R, Dewhirst M W, Yuan F, Chilkoti A. Tumor vascular permeability, accumulation, and penetration of macromolecular drug carriers. Journal of the National Cancer Institute. 2006; 98:335-44.
15. Gligorijevic B, Bergman A, Condeelis J. Multiparametric classification links tumor microenvironments with tumor cell phenotype. PLOS biology. 2014; 12:e1001995.
16. Hashizume H, Baluk P, Morikawa S, McLean J W, Thurston G, Roberge S, et al. Openings between defective endothelial cells explain tumor vessel leakiness. Am J Pathol. 2000; 156:1363-80.
17. Leung D W, Cachianes G, Kuang W J, Goeddel D V, Ferrara N. Vascular endothelial growth factor is a secreted angiogenic mitogen. Science. 1989; 246:1306-9.
18. Burnett S H, Kershen E J, Zhang J, Zeng L, Straley S C, Kaplan A M, et al. Conditional macrophage ablation in transgenic mice expressing a Fas-based suicide gene. J Leukoc Biol. 2004; 75:612-23.
19. Priceman S J, Sung J L, Shaposhnik Z, Burton J B, Torres-Collado A X, Moughon D L, et al. Targeting distinct tumor-infiltrating myeloid cells by inhibiting CSF-1 receptor: combating tumor evasion of antiangiogenic therapy. Blood. 2010; 115:1461-71.
20. Pucci F, Venneri M A, Biziato D, Nonis A, Moi D, Sica A, et al. A distinguishing gene signature shared by tumor-infiltrating Tie2-expressing monocytes, blood "resident" monocytes, and embryonic macrophages suggests common functions and developmental relationships. Blood. 2009; 114:901-14.
21. Mazzieri R, Pucci F, Moi D, Zonari E, Ranghetti A, Berti A, et al. Targeting the ANG2/TIE2 axis inhibits tumor growth and metastasis by impairing angiogenesis and disabling rebounds of proangiogenic myeloid cells. Cancer Cell. 2011; 19:512-26.
22. Keskin D, Kim J, Cooke V G, Wu C C, Sugimoto H, Gu C, et al. Targeting Vascular Pericytes in Hypoxic Tumors Increases Lung Metastasis via Angiopoietin-2. Cell reports. 2015; 10:1066-81.
23. Nakayama M, Berger P. Coordination of VEGF receptor trafficking and signaling by coreceptors. Experimental Cell Research. 2013; 319:1340-7.
24. Qian B Z, Li J, Zhang H, Kitamura T, Zhang J, Campion L R, et al. CCL2 recruits inflammatory monocytes to facilitate breast-tumour metastasis. Nature. 2011; 475: 222-5.
25. Cooke V G, LeBleu V S, Keskin D, Khan Z, O'Connell J T, Teng Y, et al. Pericyte depletion results in hypoxia-associated epithelial-to-mesenchymal transition and metastasis mediated by met signaling pathway. Cancer Cell. 2012; 21:66-81.
26. Rohan T, Xue, X, Lin, H. M., Ginsberg, M., Robinson, B., Ginter, P., D'Alfonso, T., Gertler, F., Oktay, M. Glass, A., Sparano, J., Condeelis, J. and Jones, J. Tumor microenvironment of metastasis and risk of hematogenous dissemination of breast cancer. 2014; In Press.
27. Wyckoff J, Wang W, Lin E Y, Wang Y, Pixley F, Stanley E R, et al. A paracrine loop between tumor cells and macrophages is required for tumor cell migration in mammary tumors. Cancer Res. 2004; 64:7022-9.
28. Condeelis et al. Tumor microenvironment of metastasis (TMEM) and uses thereof in diagnosis, prognosis and treatment of tumors, U.S. Pat. No. 8,642,277 B2, issued Feb. 4, 2014.
29. Weis S, Cui J, Barnes L, Cheresh D. Endothelial barrier disruption by VEGF-mediated Src activity potentiates tumor cell extravasation and metastasis. The Journal of Cell Biology. 2004; 167:223-9.

30. Chen Xiao L, Nam J-O, Jean C, Lawson C, Walsh Colin T, Goka E, et al. VEGF-Induced Vascular Permeability Is Mediated by FAK. Developmental Cell. 2012; 22:146-57.
31. Wyckoff J, Gligorijevic B, Entenberg D, Segall J, Condeelis J. High-Resolution Multiphoton Imaging of Tumors In Vivo. Cold Spring S Harbor Protocols. 2011; 2011:pdb.top065904.
32. Deciphera Pharmaceuticals Presents Preclinical Data on Rebastinib and DCC-3014 at AACR Tumor Microenvironment Conference. Press Release, Mar. 17, 2014, world wide web.deciphera.com/article/deciphera-pharmaceuticals-presents-preclinical-data-rebastinib-and-dcc-3014-aacr-tumor.
33. Smith B D, Hood M M, Kaufman M D, Berger M, Flynn D L, Wise S C. Resbastinib, a small molecule TIE2 kinase inhibitor, prevents primary tumor growth and lung metastasis in the PyMT breast cancer model. Cancer Research, Feb. 1, 2013 73, B78.

What is claimed is:

1. A method of preventing or reducing tumor cell dissemination and metastasis in a subject comprising:
    receiving an identification of the subject as having tumor sites that are active in tumor cell dissemination (TMEM$^{Active}$ site), wherein the subject is identified by a method comprising:
    a) obtaining a tumor sample from the subject;
    b) performing an assay of the tumor sample to detect the presence of a macrophage and an endothelial cell, wherein the macrophage is detected by assaying for the presence of CD68 and the endothelial cell is detected by assaying for the presence of CD31; and
    c) performing an assay to detect the levels of Tie2 and VEGFA in the macrophage and VEGFA and at least one of VE-Cadherin and ZO-1 in the endothelial cell, wherein Tie2$^{Hi}$/VEGFA$^{Hi}$ macrophages having elevated levels of VEGFA relative to adjacent endothelial cells and tumor tissue and endothelial cells having low levels of at least one of VE-Cadherin and ZO-1 indicate the presence of a TMEM$^{Active}$ site; and
administering an anti-cancer therapy to the subject identified as having TMEM$^{Active}$ sites.

2. The method of claim 1, wherein the anti-cancer therapy comprises administration to the subject of a drug that inhibits TMEM function.

3. The method of claim 1, wherein the anti-cancer therapy comprises administration of a Tie2 kinase inhibitor to the subject.

* * * * *